US008003127B2

(12) United States Patent
Liversidge et al.

(10) Patent No.: US 8,003,127 B2
(45) Date of Patent: Aug. 23, 2011

(54) NANOPARTICULATE CORTICOSTEROID AND ANTIHISTAMINE FORMULATIONS METHODS OF MAKING, AND METHODS OF ADMINISTERING THEREOF

(75) Inventors: Gary Liversidge, West Chester, PA (US); Scott Jenkins, Downingtown, PA (US); H. William Bosch, Bryn Mawr, PA (US); Christian F. Wertz, Lansdale, PA (US)

(73) Assignee: Elan Pharma International Limited, Monksland, Athlone, County Westmeath (IE)

( * ) Notice: Subject to any disclaimer, the term of this patent is extended or adjusted under 35 U.S.C. 154(b) by 1153 days.

(21) Appl. No.: 11/387,068

(22) Filed: Mar. 23, 2006

(65) Prior Publication Data

US 2006/0216353 A1 Sep. 28, 2006

Related U.S. Application Data

(60) Provisional application No. 60/664,359, filed on Mar. 23, 2005.

(51) Int. Cl.
*A61K 9/14* (2006.01)
*A61K 31/55* (2006.01)
*A61K 31/56* (2006.01)

(52) U.S. Cl. ........ 424/489; 514/170; 514/171; 514/177; 514/180; 514/181; 514/217.05; 977/788; 977/904

(58) Field of Classification Search .................. 424/489; 514/170, 171, 177, 180, 181, 217.05; 977/788, 977/904
See application file for complete search history.

(56) References Cited

U.S. PATENT DOCUMENTS

| | | | |
|---|---|---|---|
| 4,783,484 A | 11/1988 | Violante et al. |
| 4,807,814 A | 2/1989 | Douche et al. |
| 4,826,689 A | 5/1989 | Violanto et al. |
| 4,997,454 A | 3/1991 | Violante et al. |
| 5,145,684 A | 9/1992 | Liversidge et al. |
| 5,298,262 A | 3/1994 | Na et al. |
| 5,302,401 A | 4/1994 | Liversidge et al. |
| 5,318,767 A | 6/1994 | Liversidge et al. |
| 5,326,552 A | 7/1994 | Na et al. |
| 5,328,404 A | 7/1994 | Bacon |
| 5,336,507 A | 8/1994 | Na et al. |
| 5,340,564 A | 8/1994 | Illig et al. |
| 5,346,702 A | 9/1994 | Na et al. |
| 5,349,957 A | 9/1994 | Yudelson |
| 5,352,459 A | 10/1994 | Hollister et al. |
| 5,399,363 A | 3/1995 | Liversidge et al. |
| 5,401,492 A | 3/1995 | Kellar et al. |
| 5,429,824 A | 7/1995 | June |
| 5,447,710 A | 9/1995 | Na et al. |
| 5,451,393 A | 9/1995 | Liversidge et al. |
| 5,466,440 A | 11/1995 | Ruddy et al. |
| 5,470,583 A | 11/1995 | Na et al. |
| 5,472,683 A | 12/1995 | Illig |
| 5,494,683 A | 2/1996 | Liversidge et al. |
| 5,500,204 A | 3/1996 | Osifo |
| 5,510,118 A | 4/1996 | Bosch et al. |
| 5,518,187 A | 5/1996 | Bruno et al. |
| 5,518,738 A | 5/1996 | Eickhoff et al. |
| 5,521,218 A | 5/1996 | Osifo |
| 5,525,328 A | 6/1996 | Bacon et al. |
| 5,534,270 A | 7/1996 | De Castro |
| 5,543,133 A | 8/1996 | Swanson et al. |
| 5,552,160 A | 9/1996 | Liversidge et al. |
| 5,560,931 A | 10/1996 | Eickhoff et al. |
| 5,560,932 A | 10/1996 | Bagchi et al. |
| 5,565,188 A | 10/1996 | Wong et al. |
| 5,569,448 A | 10/1996 | Wong et al. |
| 5,571,536 A | 11/1996 | Eickhoff et al. |
| 5,573,749 A | 11/1996 | Illig |
| 5,573,750 A | 11/1996 | Singh |
| 5,573,783 A | 11/1996 | Desieno et al. |
| 5,580,579 A | 12/1996 | Ruddy et al. |
| 5,585,108 A | 12/1996 | Ruddy et al. |
| 5,587,143 A | 12/1996 | Wong |
| 5,591,456 A | 1/1997 | Franson et al. |
| 5,593,657 A | 1/1997 | Ruddy et al. |
| 5,622,938 A | 4/1997 | Wong |
| 5,628,981 A | 5/1997 | Liversidge et al. |
| 5,643,552 A | 7/1997 | Illig |
| 5,665,331 A | 9/1997 | Bagchi et al. |
| 5,718,388 A | 2/1998 | Czekai et al. |
| 5,718,919 A | 2/1998 | Ruddy et al. |
| 5,741,522 A | 4/1998 | Violante et al. |
| 5,747,001 A | 5/1998 | Wiedmann et al. |
| 5,776,496 A | 7/1998 | Violante et al. |

(Continued)

FOREIGN PATENT DOCUMENTS

EP 0 347 779 A2 12/1989

(Continued)

OTHER PUBLICATIONS

Curran et al. "Cetrizine: A Review of its Use in Allergic Disorders," Drugs 2004, pp. 523-561.*
Merriam-Webster's Collegiate Dictionary, 10th edition, Merriam-Webster Incorporated: Springfield, Massachusetts, 1993, pp. 311.*
Drug Information Handbook, Lacy, C.; Armstrong, L. L.; Lipsy, R. J.; Lance, L. L. Drug Information Handbook, Lexi-Comp, Inc.: Cleveland, 1993, pp. 190-191,235-236, and 1060.*
Drugs: Facts and Comparisons®, Facts and Comparisons, Inc.: St. Louis, MO, 1996, pp. 188-194b.*
Waddell et al. "Intranasal sprays in the treatment of rhinitis: is one better than another?" The Journal of Laryngology & Otology, Nov. 2003, 117, pp. 843-845.*

(Continued)

*Primary Examiner* — James H Alstrum Acevedo
(74) *Attorney, Agent, or Firm* — Fox Rothschild LLP

(57) ABSTRACT

Compositions comprising a nanoparticulate corticosteroid and an antihistamine are described. The compositions are useful in the prophylaxis and chronic treatment of asthma in adults and pediatric patients and for the relief of allergic conjunctivitis, symptoms of seasonal allergic rhinitis in adults and pediatric patients. Combining an antihistamine with a nanoparticulate corticosteroid in a single formulation results in improved efficacy.

24 Claims, No Drawings

U.S. PATENT DOCUMENTS

| | | | |
|---|---|---|---|
| 5,785,049 A | 7/1998 | Smith et al. | |
| 5,834,025 A | 11/1998 | De Garavilla et al. | |
| 5,862,999 A | 1/1999 | Czekai et al. | |
| 6,045,829 A | 4/2000 | Liversidge et al. | |
| 6,068,858 A | 5/2000 | Liversidge et al. | |
| 6,153,225 A | 11/2000 | Lee et al. | |
| 6,165,506 A | 12/2000 | Jain et al. | |
| 6,221,400 B1 | 4/2001 | Liversidge et al. | |
| 6,264,922 B1 | 7/2001 | Wood et al. | |
| 6,267,989 B1 | 7/2001 | Liversidge et al. | |
| 6,270,806 B1 | 8/2001 | Liversidge et al. | |
| 6,316,029 B1 | 11/2001 | Jain et al. | |
| 6,375,986 B1 | 4/2002 | Ryde et al. | |
| 6,428,814 B1 | 8/2002 | Bosch | |
| 6,431,478 B1 | 8/2002 | Reed et al. | |
| 6,432,381 B2 | 8/2002 | Liversidge et al. | |
| 6,582,285 B2 | 6/2003 | Czekai et al. | |
| 6,592,903 B2 | 7/2003 | Ryde et al. | |
| 6,656,504 B1 | 12/2003 | Bosch et al. | |
| 6,742,734 B2 | 6/2004 | Reed et al. | |
| 6,745,962 B2 | 6/2004 | Reed et al. | |
| 6,969,529 B2 | 11/2005 | Bosch et al. | |
| 6,976,647 B2 | 12/2005 | Reed et al. | |
| 6,991,191 B2 | 1/2006 | Reed et al. | |
| 2002/0012675 A1 | 1/2002 | Jain et al. | |
| 2002/0102294 A1* | 8/2002 | Bosch et al. | 424/450 |
| 2003/0137067 A1* | 7/2003 | Cooper et al. | 264/5 |
| 2004/0180868 A1 | 9/2004 | Mullally | |

FOREIGN PATENT DOCUMENTS

| | | |
|---|---|---|
| EP | 0780127 A1 | 6/1997 |
| GB | 2 226 495 | 7/1990 |
| WO | WO 97/01337 | 1/1997 |
| WO | WO 97/13503 | 4/1997 |
| WO | WO 99/16422 | 4/1999 |
| WO | 03/105856 A1 | 12/2003 |
| WO | 2006/058022 A1 | 6/2006 |

OTHER PUBLICATIONS

Wang et al., The activity of recent anti-allergic drugs in the treatment of seasonal allergic rhinitis, Acta oto-rhino-laryngologica belg., pp. 25-32, vol. 50, 1996, 1st Trimester, Royal Belgian Society for Ear, Nose, Throat, Head and Neck Surgery, Brussels, Belgium.

Bryon, P., "*Aerosol Formulation, Generation, and Delivery Using Nonmetered Systems,*" Respiratory Drug Delivery, 144-151, 144 (CRC Press, 1989).

Fox et al., Performance of a Venturi Eductor as a Feeder in a Pneumatic Conveying System, *Powder and Bulk Engineering*, pp. 33-36 (Mar. 1988).

Lindahl et al., "Characterization of Fluids from the Stomach and Proximal Jejunum in Men and Women", *Pharmaceutical Research*, vol. 14, No. 4, pp. 497-502 (1997).

*The Merck Index, 10$^{th}$* Ed., p. 7581 (Merck & Co., Rahway, NJ, 1983).

Busse, William W., et al., Corticosteroid-sparing Effect of Azelastine in the Management of Bronchial Asthma, Am J Respir Crit Care Med, vol. 153. pp. 122-127, (1996). XP000604179.

* cited by examiner

NANOPARTICULATE CORTICOSTEROID AND ANTIHISTAMINE FORMULATIONS METHODS OF MAKING, AND METHODS OF ADMINISTERING THEREOF

FIELD OF THE INVENTION

The invention is directed to compositions comprising at least one antihistamine and at least one nanoparticulate corticosteroid, methods of making such compositions, and methods of using such compositions. The compositions are useful in the prophylaxis and chronic treatment of asthma in adults and pediatric patients and for the relief of symptoms of allergic conjunctivitis and seasonal allergic rhinitis in adults and pediatric patients.

BACKGROUND OF THE INVENTION

A. Background Regarding Antihistamines

Antihistamines have been shown to be efficacious in the treatment of the symptoms of seasonal allergic rhinitis and in the treatment of itching of the eye associated with allergic conjunctivitis. Examples of antihistamines include, but are not limited to, azelastine hydrochloride (OPTIVAR®), chlorpheniramine maleate (CHLOR-TRIMETON®, PIRITON®), brompheniramine maleate, loratadine (CLARITIN®, ALAVERT®), astemizole (HISMANAL®), diclofenac (VOLTAREN®, CATAFLAM®), terfenadine (SELDANE®) and their salts, prodrugs and esters and combinations thereof. Other examples include Allent® (containing Brompheniramine Maleate and Pseudoephedrine Hydrochloride), Andehist® Syrup (containing Brompheniramine Maleate and Pseudoephedrine Hydrochloride), Bromadrine PD® (containing Brompheniramine Maleate and Pseudoephedrine Hydrochloride), Bromadrine® (containing Brompheniramine Maleate and Pseudoephedrine Hydrochloride), Bromfed® (containing Brompheniramine Maleate and Pseudoephedrine Hydrochloride), Bromfed-PD® (containing Brompheniramine Maleate and Pseudoephedrine Hydrochloride), Bromfenex® (containing Brompheniramine Maleate and Pseudoephedrine Hydrochloride), Bromfenex® PD (containing Brompheniramine Maleate and Pseudoephedrine Hydrochloride), Bromphenirqmine-PSE® (containing Brompheniramine Maleate and Pseudoephedrine Hydrochloride), Dallergy®-JR (containing Brompheniramine Maleate and Pseudoephedrine Hydrochloride), Dexaphen® SA (containing Dexbrompheniramine Maleate and Pseudoephedrine Sulfate), Dimetapp® Cold & Fever (containing Brompheniramine Maleate, Acetaminophen, and Pseudoephedrine Hydrochloride), Dimetapp® Elixir (containing Brompheniramine Maleate and Pseudoephedrine Hydrochloride), Drixoral® Allergy/Sinus (containing Dexbrompheniramine Maleate, Acetaminophen, and Pseudoephedrine Sulfate), Drixoral® Cold & Allergy (containing Dexbrompheniramine Maleate and Pseudoephedrine Sulfate), Drixoral® Cold & Flu (containing Dexbrompheniramine Maleate, Acetaminophen, and Pseudoephedrine Sulfate), Lodrane® (containing Brompheniramine Maleate and Pseudoephedrine Hydrochloride), Lodrane® LD (containing Brompheniramine Maleate and Pseudoephedrine Hydrochloride), Respahist® (containing Brompheniramine Maleate and Pseudoephedrine Hydrochloride), Rondec® Syrup (containing Brompheniramine Maleate and Pseudoephedrine Hydrochloride), Ultrabrom®D (containing Brompheniramine Maleate and Pseudoephedrine Hydrochloride), and Ultrabrom® PD (containing Brompheniramine Maleate and Pseudoephedrine Hydrochloride).

In allergic reactions an allergen interacts with and cross-links surface IgE antibodies on mast and basophils. Once the mast cell-antibody-antigen complex is formed, a complex series of events occurs that eventually leads to cell-degranulation and the release of histamine (and other chemical mediators) from the mast cell or basophil. Once released, histamine can react with local or widespread tissues through histamine receptors.

Histamine, acting on $H_1$-receptors, produces pruritis, vasodilation, hypotension, flushing, headache, tachycardia, bronchoconstriction, increases vascular permeability, potentiates pain, and more. $H_1$-antihistamines are clinically used in the treatment of histamine-mediated allergic conditions. These indications may include allergic rhinitis, allergic conjunctivitis, allergic dermatological conditions (contact dermatitis), urticaria, angioedema, pruritus (atopic dermatitis, insect bites), anaphylactic or anaphylactoid reactions—adjunct only, nausea and vomiting (first-generation $H_1$-antihistamines), and sedation (first-generation $H_1$-antihistamines). Antihistamines can be administered topically (through the skin, nose, or eyes) or systemically, based on the nature of the allergic condition.

Adverse drug reactions are most commonly associated with the first-generation $H_1$-antihistamines. This is due to their relative lack of selectivity for the $H_1$-receptor. The most common adverse effect is sedation—this "side effect" being utilised in many over the counter (OTC) sleeping-aid preparations. Other common adverse effects in first-generation $H_1$-antihistamines include dizziness, tinnitus, blurred vision, euphoria, uncoordination, anxiety, insomnia, tremor, nausea and vomiting, constipation, diarrhoea, dry mouth, and dry cough. Infrequent adverse effects include urinary retention, palpitations, hypotension, headache, hallucination, and psychosis.

First generation antihistamines include piperoxam, ethylenediamines (mepyramine (pyrilamine), antazoline), ethanolamines (diphenhydramine, carbinoxamine, doxylamine, clemastine, and dimenhydrinate), alkylamines (pheniramine, chlorenamine (chlorpheniramine), dexchlorphenamine, brompheniramine, and triprolidine), piperazines (cyclizine, hydroxyzine, and meclizine), and tricyclics (promethazine, alimemazine (trimeprazine), cyproheptadine, and azatadine).

The newer second-generation $H_1$-antihistamines are far more selective for peripheral histamine $H_1$-receptors and, correspondingly, have a far improved tolerability profile compared to the first-generation agents. The most common adverse effects noted for second-generation agents include drowsiness, fatigue, headache, nausea and dry mouth. Second-generation antihistamines include systemic drugs (acrivastine, astemizole, cetirizine, loratadine, mizolastine, and terfenadine), topical drugs (azelastine, levocabastine, and olopatidine), Third generation antihistamines are the active enantiomer (levocetirizine, desloratadine) or metabolite (fexofenadine) derivatives of second-generation drugs intended to have increased efficacy with fewer adverse drug reactions. For example, fexofenadine is associated with a decreased risk of cardiac arrhythmia as compared to terfenadine. However, there is little evidence for any advantage of levocetirizine or desloratadine, compared to cetirizine or loratadine respectively. Such antihistamines include levocetirizine, desloratadin, and fexofenadine.

Other inhibitors of histamine release include cromoglicate (cromolyn) and nedocromil, $H_2$-receptor antagonists (cimetidine, ranitidine, and famotidine), and $H_3$- and $H_4$-receptor antagonists (thioperamide, clobenpropit, impromidine).

B. Background Regarding Corticosteroids

Corticosteroids have been shown to be effective for the maintenance treatment of asthma as prophylactic therapy, for the management of the nasal symptoms of seasonal and perennial allergic and nonallergic rhinitis in adults and pediatric patients, and for the relief of the signs and symptoms of seasonal allergic conjunctivitis.

1. Corticosteroids Generally

Corticosteroids are drugs closely related to cortisol, a hormone which is naturally produced in the adrenal cortex (the outer layer of the adrenal gland). Corticosteroid drugs include betamethasone (Celestone®), budesonide (Entocort® EC), cortisone (Cortone®), dexamethasone (Decadron®), hydrocortisone (Cortef®), methylprednisolone (Medrol®), prednisolone (Prelone®), prednisone (Cortan®, Deltasone®, Liquid Pred®, Meticorten®, Orasone®, Panasol-S®, Prednicen-M® and Sterapred®), and triamcinolone (Kenacort®, Kenalog®).

Corticosteroids act on the immune system by blocking the production of substances that trigger allergic and inflammatory actions, such as prostaglandins. However, they also impede the function of white blood cells which destroy foreign bodies and help keep the immune system functioning properly. The interference with white blood cell function yields a side effect of increased susceptibility to infection.

Corticosteroids are widely used for many conditions. Corticosteroids are versatile in their mode of application. They can be given orally, orally, injected into the vein or muscle, applied locally to the skin, or injected directly into inflamed joints. Corticosteroid drugs can also be used as ingredients contained in inhalers to treat asthma or bronchial disease and in nasal drops and sprays to treat various nasal problems. Corticosteroids can be used in conjunction with other drugs, and are prescribed for short-term and long-term use.

The potent effect of corticosteroids can result in serious side effects which mimic Cushing's disease, a malfunction of the adrenal glands resulting in an overproduction of cortisol. The list of potential side effects is long and includes increased appetite and weight gain; deposits of fat in chest, face, upper back, and stomach; water and salt retention leading to swelling and edema; high blood pressure; diabetes; black and blue marks; slowed healing of wounds; osteoporosis; cataracts; acne; muscle weakness; thinning of the skin; increased susceptibility to infection; stomach ulcers; increased sweating; mood swings; psychological problems such as depression; and adrenal suppression and crisis. Side effects can be minimized by keeping to the lowest dose possible.

2. Inhalation Corticosteroids

Inhalation corticosteroids are cortisone-like medicines. They are used to help prevent the symptoms of asthma. When used regularly every day, inhalation corticosteroids decrease the number and severity of asthma attacks. However, they will not relieve an asthma attack that has already started.

Inhaled corticosteroids work by preventing certain cells in the lungs and breathing passages from releasing substances that cause asthma symptoms. This medicine may be used with other asthma medicines, such as bronchodilators (medicines that open up narrowed breathing passages) or other corticosteroids taken by mouth. Examples of inhalation corticosteroids currently commercially available include beclomethasone (aerosol, capsules for inhalation, and powder for inhalation); beclomethasone dipropionate HFA (aerosol); budesonide (powder for inhalation and suspension for inhalation); flunisolide (aerosol); and triamcinolone (aerosol).

C. Background Regarding Nanoparticulate Active Agent Compositions

Nanoparticulate active agent compositions, first described in U.S. Pat. No. 5,145,684 ("the '684 patent"), comprise particles of a poorly soluble therapeutic or diagnostic agent having adsorbed onto or associated with the surface thereof a non-crosslinked surface stabilizer. Methods of making nanoparticulate compositions are described, for example, in U.S. Pat. Nos. 5,518,187 and 5,862,999, both for "Method of Grinding Pharmaceutical Substances;" U.S. Pat. No. 5,718,388, for "Continuous Method of Grinding Pharmaceutical Substances;" and U.S. Pat. No. 5,510,118 for "Process of Preparing Therapeutic Compositions Containing Nanoparticles."

Nanoparticulate active agent compositions are also described, for example, in U.S. Pat. No. 5,298,262 for "Use of Ionic Cloud Point Modifiers to Prevent Particle Aggregation During Sterilization;" U.S. Pat. No. 5,302,401 for "Method to Reduce Particle Size Growth During Lyophilization;" U.S. Pat. No. 5,318,767 for "X-Ray Contrast Compositions Useful in Medical Imaging;" U.S. Pat. No. 5,326,552 for "Novel Formulation For Nanoparticulate X-Ray Blood Pool Contrast Agents Using High Molecular Weight Non-ionic Surfactants;" U.S. Pat. No. 5,328,404 for "Method of X-Ray Imaging Using Iodinated Aromatic Propanedioates;" U.S. Pat. No. 5,336,507 for "Use of Charged Phospholipids to Reduce Nanoparticle Aggregation;" U.S. Pat. No. 5,340,564 for "Formulations Comprising Olin 10-G to Prevent Particle Aggregation and Increase Stability;" U.S. Pat. No. 5,346,702 for "Use of Non-Ionic Cloud Point Modifiers to Minimize Nanoparticulate Aggregation During Sterilization;" U.S. Pat. No. 5,349,957 for "Preparation and Magnetic Properties of Very Small Magnetic-Dextran Particles;" U.S. Pat. No. 5,352,459 for "Use of Purified Surface Modifiers to Prevent Particle Aggregation During Sterilization;" U.S. Pat. Nos. 5,399,363 and 5,494,683, both for "Surface Modified Anticancer Nanoparticles;" U.S. Pat. No. 5,401,492 for "Water Insoluble Non-Magnetic Manganese Particles as Magnetic Resonance Enhancement Agents;" U.S. Pat. No. 5,429,824 for "Use of Tyloxapol as a Nanoparticulate Stabilizer;" U.S. Pat. No. 5,447,710 for "Method for Making Nanoparticulate X-Ray Blood Pool Contrast Agents Using High Molecular Weight Non-ionic Surfactants;" U.S. Pat. No. 5,451,393 for "X-Ray Contrast Compositions Useful in Medical Imaging;" U.S. Pat. No. 5,466,440 for "Formulations of Oral Gastrointestinal Diagnostic X-Ray Contrast Agents in Combination with Pharmaceutically Acceptable Clays;" U.S. Pat. No. 5,470,583 for "Method of Preparing Nanoparticle Compositions Containing Charged Phospholipids to Reduce Aggregation;" U.S. Pat. No. 5,472,683 for "Nanoparticulate Diagnostic Mixed Carbamic Anhydrides as X-Ray Contrast Agents for Blood Pool and Lymphatic System Imaging;" U.S. Pat. No. 5,500,204 for "Nanoparticulate Diagnostic Dimers as X-Ray Contrast Agents for Blood Pool and Lymphatic System Imaging;" U.S. Pat. No. 5,518,738 for "Nanoparticulate NSAID Formulations;" U.S. Pat. No. 5,521,218 for "Nanoparticulate Iododipamide Derivatives for Use as X-Ray Contrast Agents;" U.S. Pat. No. 5,525,328 for "Nanoparticulate Diagnostic Diatrizoxy Ester X-Ray Contrast Agents for Blood Pool and Lymphatic System Imaging;" U.S. Pat. No. 5,543,133 for "Process of Preparing X-Ray Contrast Compositions Containing Nanoparticles;" U.S. Pat. No. 5,552,160 for "Surface Modified NSAID Nanoparticles;" U.S. Pat. No. 5,560,931 for "Formulations of Compounds as Nanoparticulate Dispersions in Digestible Oils or Fatty Acids;" U.S. Pat. No. 5,565,188 for "Polyalkylene Block Copolymers as Surface Modifiers for Nanoparticles;" U.S. Pat. No. 5,569,448 for "Sulfated Non-ionic Block Copolymer Surfactant as Stabilizer Coatings for Nanoparticle Compositions;" U.S. Pat. No.

5,571,536 for "Formulations of Compounds as Nanoparticulate Dispersions in Digestible Oils or Fatty Acids;" U.S. Pat. No. 5,573,749 for "Nanoparticulate Diagnostic Mixed Carboxylic Anydrides as X-Ray Contrast Agents for Blood Pool and Lymphatic System Imaging;" U.S. Pat. No. 5,573,750 for "Diagnostic Imaging X-Ray Contrast Agents;" U.S. Pat. No. 5,573,783 for "Redispersible Nanoparticulate Film Matrices With Protective Overcoats;" U.S. Pat. No. 5,580,579 for "Site-specific Adhesion Within the GI Tract Using Nanoparticles Stabilized by High Molecular Weight, Linear Poly(ethylene Oxide) Polymers;" U.S. Pat. No. 5,585,108 for "Formulations of Oral Gastrointestinal Therapeutic Agents in Combination with Pharmaceutically Acceptable Clays;" U.S. Pat. No. 5,587,143 for "Butylene Oxide-Ethylene Oxide Block Copolymers Surfactants as Stabilizer Coatings for Nanoparticulate Compositions;" U.S. Pat. No. 5,591,456 for "Milled Naproxen with Hydroxypropyl Cellulose as Dispersion Stabilizer;" U.S. Pat. No. 5,593,657 for "Novel Barium Salt Formulations Stabilized by Non-ionic and Anionic Stabilizers;" U.S. Pat. No. 5,622,938 for "Sugar Based Surfactant for Nanocrystals;" U.S. Pat. No. 5,628,981 for "Improved Formulations of Oral Gastrointestinal Diagnostic X-Ray Contrast Agents and Oral Gastrointestinal Therapeutic Agents;" U.S. Pat. No. 5,643,552 for "Nanoparticulate Diagnostic Mixed Carbonic Anhydrides as X-Ray Contrast Agents for Blood Pool and Lymphatic System Imaging;" U.S. Pat. No. 5,718,388 for "Continuous Method of Grinding Pharmaceutical Substances;" U.S. Pat. No. 5,718,919 for "Nanoparticles Containing the R(-)Enantiomer of Ibuprofen;" U.S. Pat. No. 5,747,001 for "Aerosols Containing Beclomethasone Nanoparticle Dispersions;" U.S. Pat. No. 5,834,025 for "Reduction of Intravenously Administered Nanoparticulate Formulation Induced Adverse Physiological Reactions;" U.S. Pat. No. 6,045,829 "Nanocrystalline Formulations of Human Immunodeficiency Virus (HIV) Protease Inhibitors Using Cellulosic Surface Stabilizers;" U.S. Pat. No. 6,068,858 for "Methods of Making Nanocrystalline Formulations of Human Immunodeficiency Virus (HIV) Protease Inhibitors Using Cellulosic Surface Stabilizers;" U.S. Pat. No. 6,153,225 for "Injectable Formulations of Nanoparticulate Naproxen;" U.S. Pat. No. 6,165,506 for "New Solid Dose Form of Nanoparticulate Naproxen;" U.S. Pat. No. 6,221,400 for "Methods of Treating Mammals Using Nanocrystalline Formulations of Human Immunodeficiency Virus (HIV) Protease Inhibitors;" U.S. Pat. No. 6,264,922 for "Nebulized Aerosols Containing Nanoparticle Dispersions;" U.S. Pat. No. 6,267,989 for "Methods for Preventing Crystal Growth and Particle Aggregation in Nanoparticle Compositions;" U.S. Pat. No. 6,270,806 for "Use of PEG-Derivatized Lipids as Surface Stabilizers for Nanoparticulate Compositions;" U.S. Pat. No. 6,316,029 for "Rapidly Disintegrating Solid Oral Dosage Form," U.S. Pat. No. 6,375,986 for "Solid Dose Nanoparticulate Compositions Comprising a Synergistic Combination of a Polymeric Surface Stabilizer and Dioctyl Sodium Sulfosuccinate;" U.S. Pat. No. 6,428,814 for "Bioadhesive Nanoparticulate Compositions Having Cationic Surface Stabilizers;" U.S. Pat. No. 6,431,478 for "Small Scale Mill;" U.S. Pat. No. 6,432,381 for "Methods for Targeting Drug Delivery to the Upper and/or Lower Gastrointestinal Tract;" U.S. Pat. No. 6,582,285 for "Apparatus for Sanitary Wet Milling;" and U.S. Pat. No. 6,592,903 for "Nanoparticulate Dispersions Comprising a Synergistic Combination of a Polymeric Surface Stabilizer and Dioctyl Sodium Sulfosuccinate;" U.S. Pat. No. 6,656,504 for "Nanoparticulate Compositions Comprising Amorphous Cyclosporine;" U.S. Pat. No. 6,742,734 for "System and Method for Milling Materials;" U.S. Pat. No. 6,745,962 for "Small Scale Mill and Method Thereof;" U.S. Pat. No. 6,811,767 for "Liquid droplet aerosols of nanoparticulate drugs;" U.S. Pat. No. 6,908,626 for "Compositions having a combination of immediate release and controlled release characteristics;" U.S. Pat. No. 6,969,529 for "Nanoparticulate compositions comprising copolymers of vinyl pyrrolidone and vinyl acetate as surface stabilizers;" U.S. Pat. No. 6,976,647 for "System and Method for Milling Materials;" and U.S. Pat. No. 6,991,191 for "Method of Using a Small Scale Mill;" all of which are specifically incorporated by reference. In addition, U.S. Patent Application No. 20020012675 A1, published on Jan. 31, 2002, for "Controlled Release Nanoparticulate Compositions," describes nanoparticulate compositions and is specifically incorporated by reference. None of these references describe compositions of nanoparticulate corticosteroid in combination with at least one antihistamine.

Amorphous small particle compositions are described, for example, in U.S. Pat. No. 4,783,484 for "Particulate Composition and Use Thereof as Antimicrobial Agent;" U.S. Pat. No. 4,826,689 for "Method for Making Uniformly Sized Particles from Water-Insoluble Organic Compounds;" U.S. Pat. No. 4,997,454 for "Method for Making Uniformly-Sized Particles From Insoluble Compounds;" U.S. Pat. No. 5,741,522 for "Ultrasmall, Non-aggregated Porous Particles of Uniform Size for Entrapping Gas Bubbles Within and Methods;" and U.S. Pat. No. 5,776,496, for "Ultrasmall Porous Particles for Enhancing Ultrasound Back Scatter" all of which are specifically incorporated herein by reference.

There is a need for compositions of improved compositions for treating asthma. Current antihistamine compositions and corticosteroid compositions have significant side effects. Compositions having improved bioavailability and lower dosing are therefore highly desirable. The present invention satisfies these needs.

SUMMARY OF THE INVENTION

The invention is directed to compositions comprising at least one nanoparticulate corticosteroid and at least one antihistamine. The nanoparticulate corticosteroid has an effective average particle size of less than about 2000 nm. The compositions can also comprise at least one surface stabilizer for the nanoparticulate corticosteroid.

The compositions are useful in the prophylaxis and chronic treatment of asthma in adults and pediatric patients and for the relief of allergic conjunctivitis and symptoms of seasonal allergic rhinitis in adults and pediatric patients. Combining an antihistamine with a nanoparticulate corticosteroid in a single formulation results in improved efficacy. In addition, patient compliance is enhanced since only one dosage form is needed.

In one embodiment of the invention, the compositions can be combined with at least one pharmaceutically acceptable excipient or carrier.

Any suitable dosage form can be used for the compositions of the invention. In another embodiment, the compositions of the invention are formulated into topical, ocular, aerosol, nasal, or injectable dosage forms.

In one embodiment of the invention, aerosol dosage forms of at least one antihistamine and at least one nanoparticulate corticosteroid are described. Such aerosol compositions enable local administration of the antihistamine and nanoparticulate corticosteroid, which results in less liver toxicity since the liver will be exposed to lower amounts of drug as compared to oral administration. The nanoparticulate corticosteroid has an effective average particle size of less than about 2000 nm. The compositions can also comprise at least one surface stabilizer for the nanoparticulate corticosteroid.

In yet another embodiment of the invention, the compositions of the invention, comprising at least one antihistamine and at least one nanoparticulate corticosteroid, can be formulated into inhalation, nasal, topical, or ocular formulations. An inhalation formulation can be a liquid dispersion aerosol or a dry powder aerosol. A liquid composition for delivery via a nebulizer or metered dose inhaler generally utilizing a composition according to the invention, comprising at least one antihistamine and at least one nanoparticulate corticosteroid, in the form of a solution, suspension, or dispersion alone, or in combination with other substances such as an excipient. A dry powder composition according to the invention can be in the form of a dry powder alone, or in combination with other substances such as an excipient. Nasal formulations can be in the form of a solution or an appropriate solvent, dispersion or suspension of a composition according to the invention. Ocular formulations can be in the form of a solution, an appropriate solvent, dispersion or suspension in a liquid phase.

Another aspect of the invention pertains to dispersions of the compositions according to the invention, comprising at least one antihistamine and at least one nanoparticulate corticosteroid, wherein the compositions are dispersed in a liquid or in a gas. The liquid dispersions comprise at least one antihistamine, at least one nanoparticulate corticosteroid, water, a dispersing agent such as an emulsifier or a surfactant and optionally, a propellant.

In another embodiment of the invention there is provided a method of preparing a nanoparticulate corticosteroid formulation. The method comprises: (1) dispersing the corticosteroid in a liquid dispersion media; and (2) mechanically reducing the particle size of the corticosteroid to an effective average particle size of less than about 2000 nm. A surface stabilizer can be added to the dispersion media either before, during, or after particle size reduction. Preferably, the pH of the liquid dispersion media is maintained within the range of from about 3 to about 8 during the size reduction process. Following particle size reduction of the corticosteroid, at least one antihistamine can be added to the nanoparticulate corticosteroid composition.

Yet another aspect of the invention provides a method of treating a mammal in need, including a human, comprising administering to the mammal a composition comprising at least one antihistamine and at least one nanoparticulate corticosteroid according to the invention. The compositions of the invention are useful in the prophylaxis and chronic treatment of asthma, bronchial disease, and nasal problems in adults and pediatric patients, and for the relief of allergic conjunctivitis and symptoms of seasonal allergic rhinitis, allergic dermatological conditions (contact dermatitis), urticaria, angioedema, pruritus (atopic dermatitis, insect bites), sedation, and anaphylactic or anaphylactoid reactions in adults and pediatric patients.

It is to be understood that both the foregoing general description and the following detailed description are exemplary and explanatory and are intended to provide further explanation of the invention as claimed. Other objects, advantages, and novel features will be readily apparent to those skilled in the art from the following detailed description of the invention.

DETAILED DESCRIPTION OF THE INVENTION

A. Overview

The compositions according to the invention comprise at least one antihistamine and at least one nanoparticulate corticosteroid. The nanoparticulate corticosteroid has an effective average particle size of less than about 2000 nm. The compositions can also comprise at least one surface stabilizer for the nanoparticulate corticosteroid.

Any antihistamine can be included in the compositions according to the invention. Exemplary antihistamines include, but are not limited to, azelastine hydrochloride, chlorpheniramine maleate, brompheniramine maleate, loratadine, astemizole, diclofenac, terfenadine and their salts, prodrugs and esters and combinations thereof.

Any corticosteroid can be used in the compositions according to the invention. Exemplary corticosteroids include, but are not limited to, fluticasone, budesonide, triamcinolone, mometasone, flunisolide, fluticasone propionate, beclomethasone dipropionate, dexamethasone, triamincinolone, beclomethasone, fluocinolone, fluocinonide, flunisolide hemihydrate, mometasone, furoate monohydrate and combinations thereof.

Advantages of the compositions of the invention comprising at least one antihistamine and at least one nanoparticulate corticosteroid as compared to conventional, non-nanoparticulate forms of corticosteroids, and over antihistamine formulations lacking a corticosteroid component, include but are not limited to: (1) increased water solubility; (2) increased bioavailability; (3) smaller dosage form size or volume due to enhanced bioavailability; (4) lower therapeutic dosages due to enhanced bioavailability; (5) reduced risk of unwanted side effects; (6) enhanced patient convenience and compliance; (7) higher dosages possible without adverse side effects; (8) more effective prophylaxis and treatment of asthma in adults and pediatric patients; and (9) more effective relief of allergic conjunctivitis and symptoms of seasonal allergic rhinitis in adults and pediatric patients.

The invention also includes compositions of the invention, comprising at least one antihistamine and at least one nanoparticulate corticosteroid, together with one or more nontoxic physiologically acceptable carriers, adjuvants, or vehicles, collectively referred to as carriers. The compositions can be formulated for parenteral injection (e.g., intravenous, intramuscular, or subcutaneous), oral administration in solid, liquid, or aerosol form, vaginal, nasal, rectal, otic, ocular, local (powders, ointments or drops), buccal, intracisternal, intraperitoneal, or topical administration, and the like.

B. Definitions

The invention is described herein using several definitions, as set forth below and throughout the application.

The term "effective average particle size of less than about 2000 nm," as used herein means that at least 50% of the corticosteroid particles have a size, by weight, of less than about 2000 nm, when measured by, for example, sedimentation field flow fractionation, photon correlation spectroscopy, light scattering, disk centrifugation, and other techniques known to those of skill in the art.

As used herein, "about" will be understood by persons of ordinary skill in the art and will vary to some extent on the context in which it is used. If there are uses of the term which are not clear to persons of ordinary skill in the art given the context in which it is used, "about" will mean up to plus or minus 10% of the particular term.

As used herein, a "stable" corticosteroid particle connotes, but is not limited to a corticosteroid particle with one or more of the following parameters: (1) the corticosteroid particles do not appreciably flocculate or agglomerate due to interparticle attractive forces or otherwise significantly increase in particle size over time; (2) the physical structure of the corticosteroid particles is not altered over time, such as by conversion from an amorphous phase to a crystalline phase; (3) the corticosteroid particles are chemically stable; and/or (4) where the corticosteroid has not been subject to a heating step at or above the melting point of the corticosteroid in the preparation of the nanoparticles of the invention.

The term "conventional" or "non-nanoparticulate" active agent or antihistamine and/or corticosteroid shall mean an active agent, such as an antihistamine and/or a corticosteroid, which is solubilized or which has an effective average particle size of greater than about 2000 nm. Nanoparticulate active agents as defined herein have an effective average particle size of less than about 2000 nm.

The phrase "poorly water soluble drugs" as used herein refers to drugs that have a solubility in water of less than about 30 mg/ml, less than about 20 mg/ml, less than about 10 mg/ml, or less than about 1 mg/ml.

As used herein, the phrase "therapeutically effective amount" means the drug dosage that provides the specific pharmacological response for which the drug is administered in a significant number of subjects in need of such treatment. It is emphasized that a therapeutically effective amount of a drug that is administered to a particular subject in a particular instance will not always be effective in treating the conditions/diseases described herein, even though such dosage is deemed to be a therapeutically effective amount by those of skill in the art.

The term "particulate" as used herein refers to a state of matter which is characterized by the presence of discrete particles, pellets, beads or granules irrespective of their size, shape or morphology. The term "multiparticulate" as used herein means a plurality of discrete, or aggregated, particles, pellets, beads, granules or mixture thereof irrespective of their size, shape or morphology.

C. Features of the Antihistamine/Nanoparticulate Corticosteroid Compositions

There are a number of enhanced pharmacological characteristics of the antihistamine/nanoparticulate corticosteroid compositions of the invention.

1. Increased Bioavailability

In one embodiment of the invention, the antihistamine/nanoparticulate corticosteroid compositions exhibit increased bioavailability at the same dose of the same active agent, and require smaller doses as compared to prior conventional, non-nanoparticulate corticosteroid compositions.

2. The Pharmacokinetic Profiles of the Antihistamine/Nanoparticulate Corticosteroid Compositions are not Affected by the Fed or Fasted State of the Subject Ingesting the Compositions In another embodiment of the invention described are antihistamine/nanoparticulate corticosteroid compositions, wherein the pharmacokinetic profile of the corticosteroid is not substantially affected by the fed or fasted state of a subject ingesting the composition. This means that there is little or no appreciable difference in the quantity of drug absorbed or the rate of corticosteroid absorption when the antihistamine/nanoparticulate corticosteroid compositions are administered in the fed versus the fasted state.

Benefits of a dosage form which substantially eliminates the effect of food include an increase in subject convenience, thereby increasing subject compliance, as the subject does not need to ensure that they are taking a dose either with or without food. This is significant, as with poor subject compliance with a corticosteroid, an increase in the medical condition for which the drug is being prescribed may be observed—i.e., an increase in allergic rhinitis.

The invention also provides antihistamine/nanoparticulate corticosteroid compositions having a desirable pharmacokinetic profile when administered to mammalian subjects. The desirable pharmacokinetic profile of the antihistamine/nanoparticulate corticosteroid compositions preferably includes, but is not limited to: (1) a $C_{max}$ for the corticosteroid, when assayed in the plasma of a mammalian subject following administration, that is greater than the $C_{max}$ for the same non-nanoparticulate corticosteroid formulation, administered at the same dosage; and/or (2) an AUC for the corticosteroid, when assayed in the plasma of a mammalian subject following administration, that is greater than the AUC for the same non-nanoparticulate corticosteroid, administered at the same dosage; and/or (3) a $T_{max}$ for the corticosteroid, when assayed in the plasma of a mammalian subject following administration, that is less than the $T_{max}$ for the same non-nanoparticulate corticosteroid, administered at the same dosage. The desirable pharmacokinetic profile, as used herein, is the pharmacokinetic profile measured after the initial dose of the corticosteroid.

In one embodiment, a preferred antihistamine/nanoparticulate corticosteroid composition exhibits in comparative pharmacokinetic testing with the same non-nanoparticulate corticosteroid, administered at the same dosage, a $T_{max}$ for the corticosteroid which is not greater than about 90%, not greater than about 80%, not greater than about 70%, not greater than about 60%, not greater than about 50%, not greater than about 30%, not greater than about 25%, not greater than about 20%, not greater than about 15%, not greater than about 10%, or not greater than about 5% of the $T_{max}$ exhibited by the non-nanoparticulate corticosteroid.

In another embodiment, the antihistamine/nanoparticulate corticosteroid compositions of the invention exhibit in comparative pharmacokinetic testing with the same non-nanoparticulate corticosteroid, administered at the same dosage, a $C_{max}$ for the corticosteroid which is at least about 50%, at least about 100%, at least about 200%, at least about 300%, at least about 400%, at least about 500%, at least about 600%, at least about 700%, at least about 800%, at least about 900%, at least about 1000%, at least about 1100%, at least about 1200%, at least about 1300%, at least about 1400%, at least about 1500%, at least about 1600%, at least about 1700%, at least about 1800%, or at least about 1900% greater than the $C_{max}$ exhibited by the non-nanoparticulate corticosteroid.

In yet another embodiment, the antihistamine/nanoparticulate corticosteroid compositions of the invention exhibit in comparative pharmacokinetic testing with the same non-nanoparticulate corticosteroid formulation, administered at the same dosage, an AUC for the corticosteroid which is at least about 25%, at least about 50%, at least about 75%, at least about 100%, at least about 125%, at least about 150%, at least about 175%, at least about 200%, at least about 225%, at least about 250%, at least about 275%, at least about 300%, at least about 350%, at least about 400%, at least about 450%, at least about 500%, at least about 550%, at least about 600%, at least about 750%, at least about 700%, at least about 750%, at least about 800%, at least about 850%, at least about 900%, at least about 950%, at least about 1000%, at least about 1050%, at least about 1100%, at least about 1150%, or at least about 1200% greater than the AUC exhibited by the non-nanoparticulate corticosteroid.

3. Bioequivalency of the Antihistamine/Nanoparticulate Corticosteroid Compositions of the Invention when Administered in the Fed Versus the Fasted State The invention also encompasses a composition comprising at least one antihistamine and at least one nanoparticulate corticosteroid in which the AUC and $C_{max}$ for the corticosteroid, when administered to a subject in a fasted state, is bioequivalent to the AUC and $C_{max}$ for the corticosteroid when administered to a subject in a fed state.

The difference in absorption of the corticosteroid of the compositions comprising the antihistamine/nanoparticulate corticosteroid when administered in the fed versus the fasted state, is preferably less than about 100%, less than about 95%, less than about 90%, less than about 85%, less than about 80%, less than about 75%, less than about 70%, less than about 65%, less than about 60%, less than about 55%, less than about 50%, less than about 45%, less than about 35%, less than about 35%, less than about 30%, less than about 25%, less than about 20%, less than about 15%, less than about 10%, less than about 5%, or less than about 3%.

In one embodiment of the invention, the invention encompasses an antihistamine/nanoparticulate corticosteroid, wherein administration of the corticosteroid component of the composition to a subject in a fasted state is bioequivalent to administration of the corticosteroid component of the composition to a subject in a fed state, in particular as defined by $C_{max}$ and AUC guidelines given by the U.S. Food and Drug Administration (USFDA) and the corresponding European regulatory agency (EMEA). Under USFDA guidelines, two products or methods are bioequivalent if the 90% Confidence Intervals (CI) for AUC and $C_{max}$ are between 0.80 to 1.25 ($T_{max}$ measurements are not relevant to bioequivalence for regulatory purposes). To show bioequivalency between two compounds or administration conditions pursuant to Europe's EMEA guidelines, the 90% CI for AUC must be between 0.80 to 1.25 and the 90% CI for $C_{max}$ must between 0.70 to 1.43.

4. Dissolution Profiles of the Antihistamine/Nanoparticulate Corticosteroid Compositions of the Invention In yet another embodiment of the invention, the antihistamine/corticosteroid compositions of the invention have unexpectedly dramatic dissolution profiles. Rapid dissolution of the antihistamine and/or the corticosteroid is preferable, as faster dissolution generally leads to faster onset of action and greater bioavailability. To improve the dissolution profile and bioavailability of the antihistamine and/or the corticosteroid, it is useful to increase the drug(s)' dissolution so that it could attain a level close to 100%.

The antihistamine/corticosteroid compositions of the invention preferably have a dissolution profile in which within about 5 minutes at least about 20% of the corticosteroid composition is dissolved. In other embodiments of the invention, at least about 30% or at least about 40% of the corticosteroid composition is dissolved within about 5 minutes. In yet other embodiments of the invention, at least about 40%, at least about 50%, at least about 60%, at least about 70%, or at least about 80% of the corticosteroid composition is dissolved within about 10 minutes. Finally, in another embodiment of the invention, at least about 70%, at least about 80%, at least about 90%, or about at least about 100% of the corticosteroid composition is dissolved within about 20 minutes.

Dissolution is preferably measured in a medium which is discriminating. Such a dissolution medium will produce two very different dissolution curves for two products having very different dissolution profiles in gastric juices, i.e., the dissolution medium is predictive of in vivo dissolution of a composition. An exemplary dissolution medium is an aqueous medium containing the surfactant sodium lauryl sulfate at 0.025 M. Determination of the amount dissolved can be carried out by spectrophotometry. The rotating blade method (European Pharmacopoeia) can be used to measure dissolution.

5. Redispersibility Profiles of the Antihistamine/Nanoparticulate Corticosteroid Compositions of the Invention In one embodiment of the invention, the antihistamine/nanoparticulate corticosteroid compositions of the invention are formulated into solid dose forms, including powders, which redisperse such that the effective average particle size of the redispersed corticosteroid particles is less than about 2 microns. This is significant, as if upon administration the antihistamine/nanoparticulate corticosteroid compositions did not redisperse to a nanoparticulate particle size for the corticosteroid component of the compositions, then the dosage form may lose the benefits afforded by formulating the corticosteroid into a nanoparticulate particle size.

Indeed, the antihistamine/nanoparticulate corticosteroid compositions of the invention benefit from the small particle size of the corticosteroid; if the corticosteroid does not redisperse into a small particle size upon administration, then "clumps" or agglomerated corticosteroid particles are formed, owing to the extremely high surface free energy of the nanoparticulate system and the thermodynamic driving force to achieve an overall reduction in free energy. With the formation of such agglomerated particles, the bioavailability of the dosage form may fall.

Moreover, the antihistamine/nanoparticulate corticosteroid compositions of the invention exhibit dramatic redispersion of the nanoparticulate corticosteroid particles upon administration to a mammal, such as a human or animal, as demonstrated by reconstitution/redispersion in a biorelevant aqueous media such that the effective average particle size of the redispersed corticosteroid particles is less than about 2 microns. Such biorelevant aqueous media can be any aqueous media that exhibit the desired ionic strength and pH, which form the basis for the biorelevance of the media. The desired pH and ionic strength are those that are representative of physiological conditions found in the human body. Such biorelevant aqueous media can be, for example, aqueous electrolyte solutions or aqueous solutions of any salt, acid, or base, or a combination thereof, which exhibit the desired pH and ionic strength.

Biorelevant pH is well known in the art. For example, in the stomach, the pH ranges from slightly less than 2 (but typically greater than 1) up to 4 or 5. In the small intestine the pH can range from 4 to 6, and in the colon it can range from 6 to 8. Biorelevant ionic strength is also well known in the art. Fasted state gastric fluid has an ionic strength of about 0.1M while fasted state intestinal fluid has an ionic strength of about 0.14. See e.g., Lindahl et al., "Characterization of Fluids from the Stomach and Proximal Jejunum in Men and Women," *Pharm. Res.*, 14 (4): 497-502 (1997).

It is believed that the pH and ionic strength of the test solution is more critical than the specific chemical content. Accordingly, appropriate pH and ionic strength values can be obtained through numerous combinations of strong acids, strong bases, salts, single or multiple conjugate acid-base pairs (i.e., weak acids and corresponding salts of that acid), monoprotic and polyprotic electrolytes, etc.

Representative electrolyte solutions can be, but are not limited to, HCl solutions, ranging in concentration from about 0.001 to about 0.1 N, and NaCl solutions, ranging in concentration from about 0.001 to about 0.1 M, and mixtures thereof. For example, electrolyte solutions can be, but are not limited to, about 0.1 N HCl or less, about 0.01 N HCl or less, about 0.001 N HCl or less, about 0.1 M NaCl or less, about 0.01 M NaCl or less, about 0.001 M NaCl or less, and mixtures thereof. Of these electrolyte solutions, 0.01 N HCl and/or 0.1 M NaCl, are most representative of fasted human physiological conditions, owing to the pH and ionic strength conditions of the proximal gastrointestinal tract.

Electrolyte concentrations of 0.001 N HCl, 0.01 N HCl, and 0.1 N HCl correspond to pH 3, pH 2, and pH 1, respectively. Thus, a 0.01 N HCl solution simulates typical acidic conditions found in the stomach. A solution of 0.1 M NaCl provides a reasonable approximation of the ionic strength conditions found throughout the body, including the gastrointestinal fluids, although concentrations higher than 0.1 M may be employed to simulate fed conditions within the human GI tract.

Exemplary solutions of salts, acids, bases or combinations thereof, which exhibit the desired pH and ionic strength, include but are not limited to phosphoric acid/phosphate salts+sodium, potassium and calcium salts of chloride, acetic acid/acetate salts+sodium, potassium and calcium salts of chloride, carbonic acid/bicarbonate salts+sodium, potassium and calcium salts of chloride, and citric acid/citrate salts+ sodium, potassium and calcium salts of chloride.

In other embodiments of the invention, the redispersed corticosteroid particles of the invention (redispersed in an aqueous, biorelevant, or any other suitable media) have an effective average particle size of less than about 2000 nm, less than about 1900 nm, less than about 1800 nm, less than about 1700 nm, less than about 1600 nm, less than about 1500 nm, less than about 1400 nm, less than about 1300 nm, less than about 1200 nm, less than about 1100 nm, less than about 1000 nm, less than about 900 nm, less than about 800 nm, less than about 700 nm, less than about 650 nm, less than about 600 nm, less than about 550 nm, less than about 500 nm, less than about 450 nm, less than about 400 nm, less than about 350 nm, less than about 300 mm, less than about 250 nm, less than about 200 nm, less than about 150 nm, less than about 100 nm, less than about 75 nm, or less than about 50 nm, as measured by light-scattering methods, microscopy, or other appropriate methods. Such methods suitable for measuring effective average particle size are known to a person of ordinary skill in the art.

Redispersibility can be tested using any suitable means known in the art. See e.g., the example sections of U.S. Pat. No. 6,375,986 for "Solid Dose Nanoparticulate Compositions Comprising a Synergistic Combination of a Polymeric Surface Stabilizer and Dioctyl Sodium Sulfosuccinate."

6. Antihistamine/Nanoparticulate Corticosteroid Compositions Used in Conjunction with Other Active Agents The antihistamine/nanoparticulate corticosteroid compositions of the invention can additionally comprise one or more compounds useful in treating asthma, seasonal rhinitis, or related conditions. The compositions of the invention can be co-formulated with such other active agents, or the compositions of the invention can be co-administered or sequentially administered in conjunction with such active agents.

D. Compositions

The invention provides compositions comprising at least one antihistamine, at least one nanoparticulate corticosteroid, and at least one surface stabilizer. The surface stabilizers are preferably adsorbed to or associated with the surface of the corticosteroid particles. Surface stabilizers useful herein do not chemically react with the corticosteroid particles or itself. Preferably, individual molecules of the surface stabilizer are essentially free of intermolecular cross-linkages. In another embodiment, the compositions of the invention can comprise two or more surface stabilizers.

The invention also includes compositions comprising at least one antihistamine and at least one nanoparticulate corticosteroid together with one or more non-toxic physiologically acceptable carriers, adjuvants, or vehicles, collectively referred to as carriers. The compositions can be formulated for administration selected from the group consisting of oral, pulmonary, rectal, opthalmic or ocular, otic, colonic, parenteral (e.g., intravenous, intramuscular, or subcutaneous), intraperitoneal injection, intracisternal, intravaginal, local, buccal, nasal, or topical administration. The compositions of the invention can also be formulated into a dosage form such as liquid dispersions, solid dispersions, liquid-filled capsule, gels, aerosols, including dry powder and liquid dispersion aerosols and pulmonary and nasal aerosols, ointments, creams, lyophilized formulations, tablets, capsules, multi-particulate filled capsule, tablet composed of multi-particulates, or compressed tablet. The compositions of the invention can also be formulated into a dosage form such as controlled release formulations, fast melt formulations, delayed release formulations, extended release formulations, pulsatile release formulations, or mixed immediate release and controlled release formulations.

The antihistamine and corticosteroid of the invention can be in a crystalline phase, amorphous phase, semi crystalline phase, semi-amorphous phase, or a combination thereof.

1. Antihistamine

Any antihistamine, salt, prodrug, ester, or combination thereof can be used in the compositions according to the invention. Examples of antihistamines include, but are not limited to, azelastine hydrochloride (OPTIVAR®), chlorpheniramine maleate (CHLOR-TRIMETON®, PIRITON®, loratadine (CLARITIN®, ALAVERT®), astemizole (HISMANAL®), diclofenac (VOLTAREN®, CATAFLAM®), terfenadine (SELDANE®), and brompheniramine maleate (e.g., Allent® (containing Brompheniramine Maleate and Pseudoephedrine Hydrochloride), Andehist® Syrup (containing Brompheniramine Maleate and Pseudoephedrine Hydrochloride), Bromadrine PD® (containing Brompheniramine Maleate and Pseudoephedrine Hydrochloride), Bromadrine® (containing Brompheniramine Maleate and Pseudoephedrine Hydrochloride), Bromfed® (containing Brompheniramine Maleate and Pseudoephedrine Hydrochloride), Bromfed-PD® (containing Brompheniramine Maleate and Pseudoephedrine Hydrochloride), Bromfenex® (containing Brompheniramine Maleate and Pseudoephedrine Hydrochloride), Bromfenex® PD (containing Brompheniramine Maleate and Pseudoephedrine Hydrochloride), Bromphenirqmine-PSE® (containing Brompheniramine Maleate and Pseudoephedrine Hydrochloride), Dallergy®-JR (containing Brompheniramine Maleate and Pseudoephedrine Hydrochloride), Dexaphen® SA (containing Dexbrompheniramine Maleate and Pseudoephedrine Sulfate), Dimetapp® Cold & Fever (containing Brompheniramine Maleate, Acetaminophen, and Pseudoephedrine Hydrochloride), Dimetapp® Elixir (containing Brompheniramine Maleate and Pseudoephedrine Hydrochloride), Drixoral® Allergy/Sinus (containing Dexbrompheniramine Maleate, Acetaminophen, and Pseudoephedrine Sulfate), Drixoral® Cold & Allergy (containing Dexbrompheniramine Maleate and Pseudoephedrine Sulfate), Drixoral® Cold & Flu (containing Dexbrompheniramine Maleate, Acetaminophen, and Pseudoephedrine Sulfate), Lodrane® (containing Brompheniramine Maleate and Pseudoephedrine Hydrochloride), Lodrane® LD (containing Brompheniramine Maleate and Pseudoephedrine Hydrochloride), Respahist® (containing Brompheniramine Maleate and Pseudoephedrine Hydrochloride), Rondec® Syrup (containing Brompheniramine Maleate and Pseudoephedrine Hydrochloride), Ultrabrom® (containing Brompheniramine Maleate and Pseudoephedrine Hydrochloride), Ultrabrom® PD (containing Brompheniramine Maleate and Pseudoephedrine Hydrochloride).

Additional antihistamines include: (i) first generation antihistamines, including piperoxam, ethylenediamines (mepyramine (pyrilamine), antazoline), ethanolamines (diphenhydramine, carbinoxamine, doxylamine, clemastine, and dimenhydrinate), alkylamines (pheniramine, chloreenamine (chlorpheniramine), dexchlorphenamine, brompheniramine, and triprolidine), piperazines (cyclizine, hydroxyzine, and meclizine), tricyclics (promethazine, alimemazine (trimeprazine), cyproheptadine, and azatadine); (ii) second-generation $H_1$-antihistamines, including acrivastine, astemizole, cetirizine, loratadine, mizolastine, terfenadine, azelastine, levocabastine, and olopatidine; (iii) third generation antihistaminesm, including levocetirizine, desloratadine, and fexofenadine; (iv) other inhibitors of histamine release, including cromoglicate (cromolyn) and nedocromil, $H_2$-receptor antagonists (cimetidine, ranitidine, and famotidine), and $H_3$- and $H_4$-receptor antagonists (thioperamide, clobenpropit, impromidine).

2. Corticosteroids

Any corticosteroid can be used in the compositions according to the invention. Exemplary corticosteroids include, but are not limited to, fluticasone, fluticasone propionate, budesonide, triamcinolone, triamcinolone acetonide, mometasone, flunisolide, flunisolide hemihydrate, dexamethasone, triamincinolone, beclomethasone, beclomethasone dipropionate, fluocinolone, fluocinonide, betamethasone, mometasone, mometasone furoate monohydrate, cortisone, hydrocortisone, methylprednisolone, prednisolone, prednisone, and combinations thereof.

3. Surface Stabilizers

Combinations of more than one surface stabilizer can be used in the compositions comprising at least one antihistamine and at least one nanoparticulate corticosteroid of the invention. Suitable surface stabilizers include, but are not limited to, known organic and inorganic pharmaceutical excipients. Such excipients include various polymers, low molecular weight oligomers, natural products, and surfactants. Surface stabilizers include nonionic, ionic, anionic, cationic, and zwitterionic surfactants.

Representative examples of surface stabilizers include but are not limited to hydroxypropyl methylcellulose (now known as hypromellose), hydroxypropylcellulose, polyvinylpyrrolidone, sodium lauryl sulfate, dioctylsulfosuccinate, gelatin, casein, lecithin (phosphatides), dextran, gum acacia, cholesterol, tragacanth, stearic acid, benzalkonium chloride, calcium stearate, glycerol monostearate, cetostearyl alcohol, cetomacrogol emulsifying wax, sorbitan esters, polyoxyethylene alkyl ethers (e.g., macrogol ethers such as cetomacrogol 1000), polyoxyethylene castor oil derivatives, polyoxyethylene sorbitan fatty acid esters (e.g., the commercially available Tweens® such as e.g., Tween 20® and Tween 80® (ICI Speciality Chemicals)); polyethylene glycols (e.g., Carbowaxes 3550® and 934® (Union Carbide)), polyoxyethylene stearates, colloidal silicon dioxide, phosphates, carboxymethylcellulose calcium, carboxymethylcellulose sodium, methylcellulose, hydroxyethylcellulose, hypromellose phthalate, noncrystalline cellulose, magnesium aluminum silicate, triethanolamine, polyvinyl alcohol (PVA), 4-(1, 1,3,3-tetramethylbutyl)-phenol polymer with ethylene oxide and formaldehyde (also known as tyloxapol, superione, and triton), poloxamers (e.g., Pluronics F68® and F108®, which are block copolymers of ethylene oxide and propylene oxide); poloxamines (e.g., Tetronic 908®, also known as Poloxamine 908®, which is a tetrafunctional block copolymer derived from sequential addition of propylene oxide and ethylene oxide to ethylenediamine (BASF Wyandotte Corporation, Parsippany, N.J.)); Tetronic 1508® (T-1508) (BASF Wyandotte Corporation), Tritons X-200®, which is an alkyl aryl polyether sulfonate (Rohm and Haas); Crodestas F-110®, which is a mixture of sucrose stearate and sucrose distearate (Croda Inc.); p-isononylphenoxypoly-(glycidol), also known as Olin-1OG® or Surfactant 10-G® (Olin Chemicals, Stamford, Conn.); Crodestas SL-40® (Croda, Inc.); and SA9OHCO, which is C18H37CH2(CON(CH3)-CH2(CHOH)4(CH20H)2 (Eastman Kodak Co.); decanoyl-N-methylglucamide; n-decyl (-D-glucopyranoside; n-decyl (-D-maltopyranoside; n-dodecyl (-D-glucopyranoside; n-dodecyl (-D-maltoside; heptanoyl-N-methylglucamide; n-heptyl-(-D-glucopyranoside; n-heptyl (-D-thioglucoside; n-hexyl (-D-glucopyranoside; nonanoyl-N-methylglucamide; n-noyl (-D-glucopyranoside; octanoyl-N-methylglucamide; n-octyl-(-D-glucopyranoside; octyl (-D-thioglucopyranoside; PEG-phospholipid, PEG-cholesterol, PEG-cholesterol derivative, PEG-vitamin A, PEG-vitamin E, lysozyme, random copolymers of vinyl pyrrolidone and vinyl acetate, lysozyme, and the like.

Examples of useful cationic surface stabilizers include, but are not limited to, polymers, biopolymers, polysaccharides, cellulosics, alginates, phospholipids, and nonpolymeric compounds, such as zwitterionic stabilizers, poly-n-methylpyridinium, anthryul pyridinium chloride, cationic phospholipids, chitosan, polylysine, polyvinylimidazole, polybrene, polymethylmethacrylate trimethylammoniumbromide bromide (PMMTMABr), hexyldesyltrimethylammonium bromide (HDMAB), and polyvinylpyrrolidone-2-dimethylaminoethyl methacrylate dimethyl sulfate. Other useful cationic stabilizers include, but are not limited to, cationic lipids, sulfonium, phosphonium, and quarternary ammonium compounds, such as stearyltrimethylammonium chloride, benzyl-di(2-chloroethyl)ethylammonium bromide, coconut trimethyl ammonium chloride or bromide, coconut methyl dihydroxyethyl ammonium chloride or bromide, decyl triethyl ammonium chloride, decyl dimethyl hydroxyethyl ammonium chloride or bromide, C12-15dimethyl hydroxyethyl ammonium chloride or bromide, coconut dimethyl hydroxyethyl ammonium chloride or bromide, myristyl trimethyl ammonium methyl sulfate, lauryl dimethyl benzyl ammonium chloride or bromide, lauryl dimethyl (ethenoxy)4 ammonium chloride or bromide, N-alkyl (C12-18)dimethyl-benzyl ammonium chloride, N-alkyl (C14-18)dimethyl-benzyl ammonium chloride, N-tetradecylidmethylbenzyl ammonium chloride monohydrate, dimethyl didecyl ammonium chloride, N-alkyl and (C12-14) dimethyl 1-napthylmethyl ammonium chloride, trimethylammonium halide, alkyl-trimethylammonium salts and dialkyl-dimethylammonium salts, lauryl trimethyl ammonium chloride, ethoxylated alkyamidoalkyldialkylammonium salt and/or an ethoxylated trialkyl ammonium salt, dialkylbenzene dialkylammonium chloride, N-didecyldimethyl ammonium chloride, N-tetradecyldimethylbenzyl ammonium, chloride monohydrate, N-alkyl (C12-14) dimethyl 1-naphthylmethyl ammonium chloride and dodecyldimethylbenzyl ammonium chloride, dialkyl benzenealkyl ammonium chloride, lauryl trimethyl ammonium chloride, alkylbenzyl methyl ammonium chloride, alkyl benzyl dimethyl ammonium bromide, C12, C15, C17 trimethyl ammonium bromides, dodecylbenzyl triethyl ammonium chloride, poly-diallyldimethylammonium chloride (DADMAC), dimethyl ammonium chlorides, alkyldimethylammonium halogenides, tricetyl methyl ammonium chloride, decyltrimethylammonium bromide, dodecyltriethylammonium bromide, tetradecyltrimethylammonium bromide, methyl trioctylammonium chloride (ALIQUAT 336), POLYQUAT, tetrabutylammonium bromide, benzyl trimethylammonium bromide, choline esters (such as choline esters of fatty acids), benzalkonium chloride, stearalkonium chloride compounds (such as stearyltrimonium chloride and distearyldimonium chloride), cetyl pyridinium bromide or chloride, halide salts of quaternized polyoxyethylalkylamines, MIRAPOL and ALKAQUAT (Alkaril Chemical Company), alkyl pyridinium salts; amines, such as alkylamines, dialkylamines, alkanolamines, polyethylenepolyamines, N,N-dialkylaminoalkyl acrylates, and vinyl pyridine, amine salts, such as lauryl amine acetate, stearyl amine acetate, alkylpyridinium salt, and alkylimidazolium salt, and amine oxides; imide azolinium salts; protonated quaternary acrylamides; methylated quaternary polymers, such as poly [diallyl dimethylammonium chloride] and poly-[N-methyl vinyl pyridinium chloride]; and cationic guar.

Such exemplary cationic surface stabilizers and other useful cationic surface stabilizers are described in J. Cross and E. Singer, Cationic Surfactants: Analytical and Biological Evaluation (Marcel Dekker, 1994); P. and D. Rubingh (Editor), Cationic Surfactants: Physical Chemistry (Marcel Dekker, 1991); and J. Richmond, Cationic Surfactants: Organic Chemistry, (Marcel Dekker, 1990).

Nonpolymeric surface stabilizers are any nonpolymeric compound, such benzalkonium chloride, a carbonium compound, a phosphonium compound, an oxonium compound, a halonium compound, a cationic organometallic compound, a quarternary phosphorous compound, a pyridinium compound, an anilinium compound, an ammonium compound, a hydroxylammonium compound, a primary ammonium compound, a secondary ammonium compound, a tertiary ammonium compound, and quarternary ammonium compounds of the formula NR1R2R3R4(+). For compounds of the formula NR1R2R3R4(+):

(i) none of R1-R4 are CH3;
(ii) one of R1-R4 is CH3;
(iii) three of R1-R4 are CH3;
(iv) all of R1-R4 are CH3;
(v) two of R1-R4 are CH3, one of R1-R4 is $C_6H_5CH2$, and one of R1-R4 is an alkyl chain of seven carbon atoms or less;
(vi) two of R1-R4 are CH3, one of R1-R4 is $C_6H_5CH2$, and one of R1-R4 is an alkyl chain of nineteen carbon atoms or more;
(vii) two of R1-R4 are CH3 and one of R1-R4 is the group $C_6H_5(CH2)n$, where n>1;
(viii) two of R1-R4 are CH3, one of R1-R4 is $C_6H_5CH2$, and one of R1-R4 comprises at least one heteroatom;
(ix) two of R1-R4 are CH3, one of R1-R4 is $C_6H_5CH2$, and one of R1-R4 comprises at least one halogen;
(x) two of R1-R4 are CH3, one of R1-R4 is $C_6H_5CH2$, and one of R1-R4 comprises at least one cyclic fragment;
(xi) two of R1-R4 are CH3 and one of R1-R4 is a phenyl ring; or
(xii) two of R1-R4 are CH3 and two of R1-R4 are purely aliphatic fragments.

Such compounds include, but are not limited to, behenalkonium chloride, benzethonium chloride, cetylpyridinium chloride, behentrimonium chloride, lauralkonium chloride, cetalkonium chloride, cetrimonium bromide, cetrimonium chloride, cethylamine hydrofluoride, chlorallylmethenamine chloride (Quaternium-15), distearyldimonium chloride (Quaternium-5), dodecyl dimethyl ethylbenzyl ammonium chloride (Quaternium-14), Quaternium-22, Quaternium-26, Quaternium-18 hectorite, dimethylaminoethylchloride hydrochloride, cysteine hydrochloride, diethanolammonium POE (10) oletyl ether phosphate, diethanolammonium POE (3) oleyl ether phosphate, tallow alkonium chloride, dimethyl dioctadecylammoniumbentonite, stearalkonium chloride, domiphen bromide, denatonium benzoate, myristalkonium chloride, laurtrimonium chloride, ethylenediamine dihydrochloride, guanidine hydrochloride, pyridoxine HCl, iofetamine hydrochloride, meglumine hydrochloride, methylbenzethonium chloride, myrtrimonium bromide, oleyltrimonium chloride, polyquaternium-1, procainehydrochloride, cocobetaine, stearalkonium bentonite, stearalkoniumhectorite, stearyl trihydroxyethyl propylenediamine dihydrofluoride, tallowtrimonium chloride, and hexadecyltrimethyl ammonium bromide.

Most of these surface stabilizers are known pharmaceutical excipients and are described in detail in the *Handbook of Pharmaceutical Excipients*, published jointly by the American Pharmaceutical Association and The Pharmaceutical Society of Great Britain (The Pharmaceutical Press, 2000), specifically incorporated herein by reference.

Povidone Polymers

Povidone polymers are exemplary surface stabilizers for use in formulating an injectable antihistamine/nanoparticulate corticosteroid formulation. Povidone polymers, also known as polyvidon(e), povidonum, PVP, and polyvinylpyrrolidone, are sold under the trade names Kollidon® (BASF Corp.) and Plasdone® (ISP Technologies, Inc.). They are polydisperse macromolecular molecules, with a chemical name of 1-ethenyl-2-pyrrolidinone polymers and 1-vinyl-2-pyrrolidinone polymers. Povidone polymers are produced commercially as a series of products having mean molecular weights ranging from about 10,000 to about 700,000 daltons. To be useful as a surface modifier for a drug compound to be administered to a mammal, the povidone polymer must have a molecular weight of less than about 40,000 daltons, as a molecular weight of greater than 40,000 daltons would have difficulty clearing the body.

Povidone polymers are prepared by, for example, Reppe's process, comprising: (1) obtaining 1,4-butanediol from acetylene and formaldehyde by the Reppe butadiene synthesis; (2) dehydrogenating the 1,4-butanediol over copper at 200° to form γ-butyrolactone; and (3) reacting γ-butyrolactone with ammonia to yield pyrrolidone. Subsequent treatment with acetylene gives the vinyl pyrrolidone monomer. Polymerization is carried out by heating in the presence of $H_2O$ and $NH_3$. See *The Merck Index*, $10^{th}$ Edition, pp. 7581 (Merck & Co., Rahway, N.J., 1983).

The manufacturing process for povidone polymers produces polymers containing molecules of unequal chain length, and thus different molecular weights. The molecular weights of the molecules vary about a mean or average for each particular commercially available grade. Because it is difficult to determine the polymer's molecular weight directly, the most widely used method of classifying various molecular weight grades is by K-values, based on viscosity measurements. The K-values of various grades of povidone polymers represent a function of the average molecular weight, and are derived from viscosity measurements and calculated according to Fikentscher's formula.

The weight-average of the molecular weight, Mw, is determined by methods that measure the weights of the individual molecules, such as by light scattering. Table 1 provides molecular weight data for several commercially available povidone polymers, all of which are soluble.

TABLE 1

| Povidone | K-Value | Mv (Daltons)** | Mw (Daltons)** | Mn (Daltons)** |
|---|---|---|---|---|
| Plasdone C-15 ® | 17 ± 1 | 7,000 | 10,500 | 3,000 |
| Plasdone C-30 ® | 30.5 ± 1.5 | 38,000 | 62,500* | 16,500 |
| Kollidon 12 PF ® | 11-14 | 3,900 | 2,000-3,000 | 1,300 |
| Kollidon 17 PF ® | 16-18 | 9,300 | 7,000-11,000 | 2,500 |

TABLE 1-continued

| Povidone | K-Value | Mv (Daltons)** | Mw (Daltons)** | Mn (Daltons)** |
|---|---|---|---|---|
| Kollidon 25® | 24-32 | 25,700 | 28,000-34,000 | 6,000 |

*Because the molecular weight is greater than 40,000 daltons, this povidone polymer is not useful as a surface stabilizer for a drug compound to be administered parenterally (i.e., injected).
**Mv is the viscosity-average molecular weight, Mn is the number-average molecular weight, and Mw is the weight average molecular weight. Mw and Mn were determined by light scattering and ultra-centrifugation, and Mv was determined by viscosity measurements.

Based on the data provided in Table 1, exemplary useful commercially available povidone polymers for injectable formulations include, but are not limited to, Plasdone C-15®, Kollidon 12 PF®, Kollidon 17 PF®, and Kollidon 25®.

4. Nanoparticulate Corticosteroid Particle Size

As used herein, particle size is determined on the basis of the weight average particle size as measured by conventional particle size measuring techniques well known to those skilled in the art. Such techniques include, for example, sedimentation field flow fractionation, photon correlation spectroscopy, light scattering, and disk centrifugation.

The compositions of the invention comprise at least one nanoparticulate corticosteroid having an effective average particle size of less than about 2000 nm (i.e., 2 microns). In other embodiments of the invention, the corticosteroid nanoparticles have an effective average particle size of less than about 1900 nm, less than about 1800 nm, less than about 1700 nm, less than about 1600 nm, less than about 1500 nm, less than about 1400 nm, less than about 1300 nm, less than about 1200 nm, less than about 1100 nm, less than about 1000 nm, less than about 900 nm, less than about 800 nm, less than about 700 nm, less than about 650 nm, less than about 600 nm, less than about 550 nm, less than about 500 nm, less than about 450 nm, less than about 400 nm, less than about 350 nm, less than about 300 nm, less than about 250 nm, less than about 200 nm, less than about 150 nm, less than about 100 nm, less than about 75 nm, or less than about 50 nm, as measured by light-scattering methods, microscopy, or other appropriate methods.

An "effective average particle size of less than about 2000 nm" means that at least 50% of the corticosteroid particles have a particle size less than the effective average, by weight, i.e., less than about 2000 nm. If the "effective average particle size" is less than about 1900 nm, then at least about 50% of the corticosteroid particles have a size of less than about 1900 nm, when measured by the above-noted techniques. The same is true for the other particle sizes referenced above. In other embodiments, at least about 60%, at least about 70%, at least about 80%, at least about 90%, at least about 95%, or at least about 99% of the corticosteroid particles have a particle size less than the effective average, i.e., less than about 2000 nm, less than about 1900 nm, less than about 1800 nm, etc.

In the invention, the value for D50 of a nanoparticulate corticosteroid composition is the particle size below which 50% of the corticosteroid particles fall, by weight. Similarly, D90 and D95 are the particle sizes below which 90% and 95%, respectively, of the corticosteroid particles fall, by weight.

5. Concentration of Antihistamine, Nanoparticulate Corticosteroid, and Surface Stabilizers The relative amounts of antihistamine, corticosteroid, and at least one surface stabilizer can vary widely. The optimal amount of the individual components depends upon, for example, the particular antihistamine selected, the particular corticosteroid selected, the physical and chemical attributes of the surface stabilizer(s) selected, such as the hydrophilic lipophilic balance (HLB), melting point, and the surface tension of water solutions of the stabilizer, etc.

Preferably, the concentration of the corticosteroid can vary from about 99.5% to about 0.001%, from about 95% to about 0.1%, or from about 90% to about 0.5%, by weight, based on the total combined weight of the corticosteroid and at least one surface stabilizer, not including other excipients. Higher concentrations of the active ingredient are generally preferred from a dose and cost efficiency standpoint.

Preferably, the concentration of surface stabilizer for the corticosteroid can vary from about 0.5% to about 99.999%, from about 5.0% to about 99.9%, or from about 10% to about 99.5%, by weight, based on the total combined dry weight of the corticosteroid and at least one surface stabilizer, not including other excipients.

In one embodiment of the invention, and particularly for aerosol compositions, the amount of the at least one antihistamine in the compositions according to the invention can range from about 0.1 to about 10%, by weight, and the amount of the at least one corticosteroid can range from about 0.01 to about 10% by weight.

When formulated in an aerosol, the compositions of the invention can comprise an antihistamine at a concentration selected from the group consisting of about 10 mg/mL or more, about 100 mg/mL or more, about 200 mg/mL or more, about 400 mg/mL or more, or about 600 mg/mL.

When formulated as an aerosol, the compositions of the invention can comprise a corticosteroid at a concentration selected from the group consisting of about 10 mg/mL or more, about 100 mg/mL or more, about 200 mg/mL or more, about 400 mg/mL or more, or about 600 mg/mL.

6. Other Pharmaceutical Excipients

Pharmaceutical compositions of the invention may also comprise one or more binding agents, filling agents, lubricating agents, suspending agents, sweeteners, flavoring agents, preservatives, buffers, wetting agents, disintegrants, effervescent agents, and other excipients depending upon the route of administration and the dosage form desired. Such excipients are well known in the art.

Examples of filling agents are lactose monohydrate, lactose anhydrous, and various starches; examples of binding agents are various celluloses and cross-linked polyvinylpyrrolidone, microcrystalline cellulose, such as Avicel® PH101 and Avicel® PH102, microcrystalline cellulose, and silicified microcrystalline cellulose (ProSolv SMCC™).

Suitable lubricants, including agents that act on the flowability of the powder to be compressed, are colloidal silicon dioxide, such as Aerosil® 200, talc, stearic acid, magnesium stearate, calcium stearate, and silica gel.

Examples of sweeteners are any natural or artificial sweetener, such as sucrose, xylitol, sodium saccharin, cyclamate, aspartame, and acsulfame. Examples of flavoring agents are Magnasweet® (trademark of MAFCO), bubble gum flavor, and fruit flavors, and the like.

Examples of preservatives are potassium sorbate, methylparaben, propylparaben, benzoic acid and its salts, other esters of parahydroxybenzoic acid such as butylparaben, alcohols such as ethyl or benzyl alcohol, phenolic compounds such as phenol, and quarternary compounds such as benzalkonium chloride.

Suitable diluents include pharmaceutically acceptable inert fillers, such as microcrystalline cellulose, lactose, dibasic calcium phosphate, saccharides, and/or mixtures of any of the foregoing. Examples of diluents include microcrystalline cellulose, such as Avicele PH101 and Avicel® PH102; lactose such as lactose monohydrate, lactose anhydrous, and Pharmatose® DCL21; dibasic calcium phosphate such as Emcompress®; mannitol; starch; sorbitol; sucrose; and glucose.

Suitable disintegrants include lightly crosslinked polyvinyl pyrrolidone, corn starch, potato starch, maize starch, and modified starches, croscarmellose sodium, cross-povidone, sodium starch glycolate, and mixtures thereof.

Examples of effervescent agents are effervescent couples, such as an organic acid and a carbonate or bicarbonate. Suitable organic acids include, for example, citric, tartaric, malic, fumaric, adipic, succinic, and alginic acids and anhydrides and acid salts. Suitable carbonates and bicarbonates include, for example, sodium carbonate, sodium bicarbonate, potassium carbonate, potassium bicarbonate, magnesium carbonate, sodium glycine carbonate, L-lysine carbonate, and arginine carbonate. Alternatively, only the sodium bicarbonate component of the effervescent couple may be present.

7. Aerosol Dosage Forms of Antihistamine/Nanoparticulate Corticosteroid Compositions of the Invention The invention encompasses dry powder aerosol of the antihistamine/nanoparticulate corticosteroid compositions of the invention and liquid dispersion aerosols of the antihistamine/nanoparticulate corticosteroid compositions of the invention.

In one embodiment of the invention, the aerosol droplets comprising the antihistamine/nanoparticulate corticosteroid compositions of the invention for aqueous dispersion aerosols, or the dry powder aggregates comprising the antihistamine/nanoparticulate corticosteroid compositions of the invention for dry powder aerosols, have a mass media aerodynamic diameter of less than or equal to about 100 microns. In other embodiments of the invention, the aerosol droplets comprising the antihistamine/nanoparticulate corticosteroid compositions of the invention for aqueous dispersion aerosols, or the dry powder aggregates comprising the antihistamine/nanoparticulate corticosteroid compositions of the invention for dry powder aerosols, have a mass media aerodynamic diameter (MMAD) of (1) about 30 to about 60 microns; (2) about 0.1 to about 10 microns; (3) about 2 to about 6 microns; or (4) less than about 2 microns.

Using the compositions of the invention, poorly water soluble or essentially water-insoluble corticosteroids can be delivered to the deep lung (as well as to the upper lung). This is either not possible or extremely difficult using aerosol formulations of micronized corticosteroids. Deep lung delivery requires a MMAD of less than or equal to about 2 microns. A drug particle having such an aerodynamic diameter and a density of about 1 will have a geometric diameter of less than or equal to about 2 microns. The relationship between aerodynamic diameters and geometric particle sizes is represented by the following equation:

$$\text{Aerodynamic diameter} = \text{geometric diameter (density)}^{1/2}$$

See col. 11, lines 18-46, of Edwards et al.; and P. Byron, "Aerosol Formulation, Generation, and Delivery Using Non-metered Systems," *Respiratory Drug Delivery*, 144-151, at 145 (CRC Press, 1989). A geometric particle size of less than or equal to about 2 microns is difficult or impossible to achieve with jet milling; i.e., the process used to obtain micronized drugs. The present invention overcomes this difficulty by incorporating nanoparticulate sized corticosteroid particles into aggregates having a variety of MMAD sizes, thus allowing for targeting of drugs to various regions of the respiratory tract, including deep lung delivery.

Deep lung delivery is necessary for drugs that are intended for systemic administration because deep lung delivery allows rapid absorption of the drug into the bloodstream via the alveoli, thus enabling rapid onset of action.

Nasal formulations can be in the form of a solution of an antihistamine/nanoparticulate corticosteroid composition of the invention dispersed in an appropriate solvent or as a dispersion or suspension of the antihistamine/nanoparticulate corticosteroid composition in a liquid phase and a surface stabilizer and a dry powder. A solution is comprised of a composition according to the invention and an appropriate solvent and optionally one or more cosolvents. Water is the typical solvent. However, the composition may not be soluble in water alone in which case one or more cosolvents may have to be employed to form a solution. Suitable cosolvents include, but are not limited to, short-chained alcohols, and in particular, ethanol.

The antihistamine/nanoparticulate corticosteroid aerosols of the invention enable rapid nasal absorption. When delivered to the nasal mucosa, such aerosol compositions dissolve and are absorbed more rapidly and completely than micronized drug aerosol compositions, which may be cleared by the mucociliary mechanism prior to drug dissolution and absorption.

Nasal formulations can also be in the form of a dispersion or suspension. In these types of formulations, an antihistamine/nanoparticulate corticosteroid composition according to the invention can be in the form of a dispersion or suspension of the active agents in water with or without one or more suspending agents. Suitable suspending agents are surfactants, emulsifiers or surface modifiers and can be selected from known organic and inorganic pharmaceutical excipients. Such excipients include various polymers, low molecular weight oligomers, natural products, and surfactants.

In one embodiment of the invention, for aqueous aerosol formulations, an antihistamine/nanoparticulate corticosteroid composition according to the invention is present at a concentration of about 0.05 mg/mL up to about 600 mg/mL (concentration for each active agent). In another embodiment of the invention, for dry powder aerosol formulations, an antihistamine/nanoparticulate corticosteroid composition according to the invention is present at a concentration of about 0.05 mg/g up to about 990 mg/g (concentration for each active agent), depending on the desired dosage. Concentrated antihistamine and nanoparticulate corticosteroid aerosols, defined as comprising a composition according to the invention at a concentration of about 10 mg/mL up to about 600 mg/mL of antihistamine and about 10 mg/mL up to about 600 mg/mL of a corticosteroid for aqueous aerosol formulations, and about 10 mg/g up to about 990 mg/g of antihistamine and about 10 mg/g up to about 990 mg/g a corticosteroid for dry powder aerosol formulations, are specifically encompassed by the present invention. Such formulations provide effective delivery to appropriate areas of the lung or nasal cavities in short administration times, i.e., less than about 15 seconds as compared to administration times of up to 4 to 20 minutes as found in conventional pulmonary nebulizer therapies.

In other embodiments of the invention, the aerosol dosage form can delivery a therapeutic quantity of antihistamine and corticosteroid in a time period such as less than about 5 minutes, less than about 4 minutes, less than about 3 minutes, less than about 2 minutes, less than about 1 minute, less than about 45 seconds, less than about 30 seconds, less than about 15 seconds, or less than about 10 seconds.

a. Aqueous Aerosols of the Compositions of the Invention

One embodiment of an antihistamine/nanoparticulate corticosteroid dispersion for nasal or pulmonary administration is an aerosol. Aqueous formulations of the invention comprise colloidal dispersions of at least one antihistamine, at least one nanoparticulate corticosteroid, and at least one surface stabilizer in an aqueous vehicle which is formulated as an aerosol using air-jet or ultrasonic nebulizers. The advantages of the use of such aqueous aerosols can best be understood by comparing the sizes of nanoparticulate corticosteroid compositions according to the invention with micronized particles of such drugs and the sizes of liquid droplets produced by conventional nebulizers. Conventional micronized material is generally about 2 to about 5 microns or more in diameter and is approximately the same size as the liquid droplet size produced by medical nebulizers. In contrast, nanoparticulate corticosteroid compositions according to the invention are substantially smaller than the droplets in such an aerosol. Thus, aerosols containing nanoparticulate corticosteroid compositions according to the invention improve drug delivery efficiency. Such aerosols comprise a higher number of corticosteroid nanoparticles per unit dose, resulting in each aerosolized droplet comprising at least one drug particle (i.e., at least one corticosteroid particle).

Thus, with administration of the same dosages of compositions according to the invention more lung or nasal cavity surface area is covered by the aerosol formulation comprising antihistamine/nanoparticulate corticosteroid compositions according to the invention.

Another advantage of the use of these aqueous aerosols is that they permit water-insoluble compositions according to the invention, e.g., corticosteroids, to be delivered to the deep lung via an aqueous formulation. Conventional micronized corticosteroids are too large to reach the peripheral lung regardless of the size of the droplets produced by the nebulizer. The aqueous aerosols comprised of compositions according to the invention permit nebulizers which generate very small (about 0.5 to about 2 microns) aqueous droplets to deliver a poorly water soluble or water insoluble active agent in the form of nanoparticles, such as a corticosteroid, to the alveoli. One example of such devices is the Circular™ aerosol (Westmed Corp., Tucson, Ariz.).

Yet another advantage of the aqueous aerosols according to the invention is that ultrasonic nebulizers can be used to deliver a poorly water soluble or water-insoluble nanoparticulate corticosteroid according to the invention to the lung. Unlike conventional micronized corticosteroids, the nanoparticulate corticosteroid is readily aerosolized and shows good in vitro deposition characteristics. A specific advantage of these aqueous aerosols is that they permit water-insoluble or poorly water soluble active agents, such as corticosteroids, to be aerosolized by ultrasonic nebulizers which require nanoparticles comprised of compositions according to the invention to pass through very fine orifices to control the size of the aerosolized droplets. While conventional drug material would be expected to occlude the pores, such nanoparticulates are much smaller and can pass through the pores without difficulty.

In one embodiment of the invention, substantially all of the liquid dispersion droplets of the aqueous aerosol of the invention comprises at least one antihistamine particle, at least one nanoparticulate corticosteroid particle, or a combination thereof.

b. Dry Power Aerosols of the Compositions of the Invention

A dry powder inhalation formulation can be made by spray-drying an aqueous nanoparticulate corticosteroid dispersion according to the invention. At least one antihistamine can be added to the dispersion either before, during, or after spray drying of the nanoparticulate corticosteroid dispersion. Alternatively, dry powders comprising a nanoparticulate corticosteroid composition according to the invention can be made by freeze-drying the nanoparticulate corticosteroid dispersions of the invention. At least one antihistamine can be added to the dispersion either before, during, or after freeze drying of the nanoparticulate corticosteroid dispersion. Combinations of the spray-dried and freeze-dried nanoparticulate powders can be used in both dry powder inhalers (DPIs) and pressurized metered dose inhaler (pMDIs).

Dry powder inhalers (DPIs), which involve deaggregation and aerosolization of dry powders, normally rely upon a burst of inspired air that is drawn through the unit to deliver a drug dosage. Such devices are described in, for example, U.S. Pat. No. 4,807,814, which is directed to a pneumatic powder ejector having a suction stage and an injection stage; SU 628930 (Abstract), describing a hand-held powder disperser having an axial air flow tube; Fox et al., *Powder and Bulk Engineering*, pages 33-36 (March 1988), describing a venturi eductor having an axial air inlet tube upstream of a venturi restriction; EP 347 779, describing a hand-held powder disperser having a collapsible expansion chamber, and U.S. Pat. No. 5,785,049. The entire content of these references are incorporated herein by reference and are directed to dry powder delivery devices for drugs.

A dry powder inhalation formulation can also be delivered by means of an aerosol formulation. The powders may consist of inhalable aggregates of antihistamine/nanoparticulate corticosteroid compositions according to the invention, or of inhalable particles of a diluent which contains at least one embedded antihistamine/nanoparticulate corticosteroid composition according to the invention. Powders comprising an antihistamine/nanoparticulate corticosteroid composition according to the invention can be prepared from aqueous dispersions of nanoparticles by removing the water by spray-drying or lyophilization (freeze drying). At least one antihistamine can be added to the nanoparticulate corticosteroid dispersion either before, during, or after spray drying or freeze drying. Spray-drying is less time consuming and less expensive than freeze-drying, and therefore more cost-effective.

Dry powder aerosol delivery devices must be able to accurately, precisely, and repeatably deliver the intended amount of an antihistamine/nanoparticulate corticosteroid composition according to the invention. Moreover, such devices must be able to fully disperse the dry powder into individual particles of a respirable size.

Dry antihistamine/nanoparticulate corticosteroid compositions can be used in both DPIs and pMDIs. (Within the context of the present invention, "dry" refers to a composition having less than about 5% water.). Nanoparticulate aerosol formulations are described in U.S. Pat. No. 6,811,767 to Bosch et al. and, which is specifically incorporated herein by reference.

In one embodiment of the invention, substantially all of the aggregates of dry powder comprise at least one antihistamine particle, at least one nanoparticulate corticosteroid particle, or a combination thereof.

i. Spray-Dried Powders Comprising Antihistamine/Nanoparticulate Corticosteroid Compositions Powders comprising an antihistamine/nanoparticulate corticosteroid compositions according to the invention can be made by spray-drying aqueous dispersions of a nanoparticulate corticosteroid composition according to the invention and a surface stabilizer to form a dry powder which consists of an aggregated nanoparticulate corticosteroid composition. At least one antihistamine can be added to the nanoparticulate corticosteroid composition either before, during, or after spray drying. The aggregates can have a size of about 1 to about 2 microns which is suitable for deep lung delivery. The aggregate particle size can be increased to target alternative delivery sites, such as the upper bronchial region or nasal mucosa by increasing the concentration of a composition according to the invention in the spray-dried dispersion or by increasing the droplet size generated by the spray dryer.

Alternatively, the aqueous dispersion of a nanoparticulate corticosteroid composition according to the invention and surface stabilizer can contain a dissolved diluent such as lactose or mannitol which, when spray dried, forms inhalable diluent particles, each of which comprises at least one embedded nanoparticulate drug and surface modifier adhered thereto. The diluent nanoparticles can have a particle size of about 1 to about 2 microns, suitable for deep lung delivery. In addition, the diluent particle size can be increased to target alternate delivery sites, such as the upper bronchial region or nasal mucosa by increasing the concentration of dissolved diluent in the aqueous dispersion prior to spray drying, or by increasing the droplet size generated by the spray dryer.

Spray-dried powders can be used in DPIs or pMDIs, either alone or combined with freeze-dried antihistamine/nanoparticulate corticosteroid powder. In addition, spray-dried powders comprising an antihistamine/nanoparticulate corticosteroid composition according to the invention can be reconstituted and used in either jet or ultrasonic nebulizers to generate aqueous dispersions having respirable droplet sizes, where each droplet comprises at least one antihistamine particle, at least one nanoparticulate corticosteroid particle, or a combination thereof. Concentrated antihistamine/nanoparticulate corticosteroid dispersions may also be used in these aspects of the invention.

ii. Freeze-Dried Powders Comprising an Antihistamine/Nanoparticulate Corticosteroid Composition Antihistamine/nanoparticulate corticosteroid compositions according to the invention in the form of nanoparticle dispersions can also be freeze-dried to obtain powders suitable for nasal or pulmonary delivery. At least one antihistamine can be added to a nanoparticulate corticosteroid dispersion either before, during, or after freeze drying. Such powders may contain aggregated antihistamine/nanoparticulate corticosteroid compositions according to the invention having a surface stabilizer. Such aggregates may have sizes within a respirable range, i.e., about 2 to about 5 microns. Larger aggregate particle sizes can be obtained for targeting alternate delivery sites, such as the nasal mucosa.

Freeze dried powders of the appropriate particle size can also be obtained by freeze drying aqueous dispersions of a composition according to the invention and surface stabilizer, which additionally contain a dissolved diluent such as lactose or mannitol. In these instances the freeze dried powders consist of respirable particles of diluent, each of which contains at least one embedded antihistamine particle, at least one nanoparticulate corticosteroid particle, or a combination thereof.

Freeze-dried powders can be used in DPIs or pMIs, either alone or combined with spray-dried antihistamine/nanoparticulate corticosteroid powder. In addition, freeze-dried powders comprising an antihistamine/nanoparticulate corticosteroid composition according to the invention can be reconstituted and used in either jet or ultrasonic nebulizers to generate aqueous dispersions having respirable droplet sizes, where each droplet comprises at least one antihistamine particle, at least one nanoparticulate corticosteroid particle, or a combination thereof. Concentrated antihistamine/nanoparticulate corticosteroid dispersions may also be used in these aspects of the invention.

c. Propellant-Based Aerosols

Another embodiment of the invention is directed to a process and composition for propellant-based MDIs (metered dose inhalers) comprising antihistamine/nanoparticulate corticosteroid compositions of the invention. pMDIs (pressured metered dose inhalers) can comprise (1) discrete antihistamine particles, discrete corticosteroid nanoparticles, and surface stabilizer(s), (2) aggregates of antihistamine, nanoparticulate corticosteroid particles, and the surface stabilizer(s), (3) motive diluent particles comprising the embedded antihistamine and nanoparticulate corticosteroid particles, and surface stabilizer(s), or (4) solutions of the drugs or combinations thereof in solvents and/or propellants. pMDIs can be used for targeting the nasal cavity, the conducting airways of the lung or the alveoli. Compared to conventional formulations, the present invention affords increased delivery to the deep lung regions because the inhaled corticosteroid nanoparticles are smaller than conventional micronized material (<2 microns) and are distributed over a larger mucosal or alveolar surface area as compared to miconized drugs.

The antihistamine/nanoparticulate corticosteroid compositions utilized in pMDIs can utilize either chlorinated or non-chlorinated propellants. Concentrated aerosol solutions or antihistamine/nanoparticulate corticosteroid aerosol formulations can also be employed in pMDIs.

Ocular formulations are in the form of a solution comprised of an antihistamine/nanoparticulate corticosteroid composition according to the invention in an appropriate solvent or a dispersion or suspension thereof in a liquid phase and a stabilizer, details of which are set forth above.

E. Methods of Making Antihistamine/Nanoparticulate Corticosteroid Formulations

Antihistamine/nanoparticulate corticosteroid compositions can be made using any suitable method known in the art. Methods of making nanoparticulate active agent compositions include, for example, milling, homogenization, precipitation, or supercritical fluid particle generation techniques. Exemplary methods of making nanoparticulate active agent compositions are described in U.S. Pat. No. 5,145,684. Methods of making nanoparticulate active agent compositions are also described in U.S. Pat. No. 5,518,187 for "Method of Grinding Pharmaceutical Substances;" U.S. Pat. No. 5,718,388 for "Continuous Method of Grinding Pharmaceutical Substances;" U.S. Pat. No. 5,862,999 for "Method of Grinding Pharmaceutical Substances;" U.S. Pat. No. 5,665,331 for "Co-Microprecipitation of Nanoparticulate Pharmaceutical Agents with Crystal Growth Modifiers;" U.S. Pat. No. 5,662,883 for "Co-Microprecipitation of Nanoparticulate Pharmaceutical Agents with Crystal Growth Modifiers;" U.S. Pat. No. 5,560,932 for "Microprecipitation of Nanoparticulate Pharmaceutical Agents;" U.S. Pat. No. 5,543,133 for "Process of Preparing X-Ray Contrast Compositions Containing Nanoparticles;" U.S. Pat. No. 5,534,270 for "Method of Preparing Stable Drug Nanoparticles;" U.S. Pat. No. 5,510,118 for "Process of Preparing Therapeutic Compositions Containing Nanoparticles;" and U.S. Pat. No. 5,470,583 for "Method of Preparing Nanoparticle Compositions Containing Charged Phospholipids to Reduce Aggregation," all of which are specifically incorporated herein by reference.

The resultant nanoparticulate corticosteroid compositions or dispersions can be combined with at least one antihistamine and then utilized in solid, semi-solid, or liquid dosage formulations, such as liquid dispersions, gels, aerosols, ointments, creams, controlled release formulations, fast melt formulations, lyophilized formulations, tablets, capsules, delayed release formulations, extended release formulations, pulsatile release formulations, mixed immediate release and controlled release formulations, etc.

In another aspect of the invention there is provided a method of preparing the antihistamine/nanoparticulate corticosteroid formulations of the invention. The method comprises the steps of: (1) dispersing the desired dosage amount of a corticosteroid in a liquid dispersion media in which the drug is poorly soluble; and (2) mechanically reducing the particle size of the corticosteroid to an effective average particle size of less than about 2000 nm. A surface stabilizer can be added to the dispersion media either before, during, or after particle size reduction of the corticosteroid. The liquid dispersion medium can be maintained at a physiologic pH, for example, within the range of from about 3.0 to about 8.0 during the size reduction process; more preferably within the range of from about 5.0 to about 7.5 during the size reduction process. Preferably, the dispersion media used for the size reduction process is aqueous, although any dispersion media in which the active ingredient is poorly soluble can be used, such as safflower oil, ethanol, t-butanol, glycerin, polyethylene glycol (PEG), hexane, or glycol. Following particle size reduction of the at least one corticosteroid, at least one antihistamine is added to the composition.

Using a particle size reduction method, the particle size of the corticosteroid is reduced to an effective average particle size of less than about 2000 nm. Effective methods of providing mechanical force for particle size reduction of the corticosteroid include ball milling, media milling, and homogenization, for example, with a Microfluidizer® (Microfluidics Corp.). Ball milling is a low energy milling process that uses milling media, drug, stabilizer, and liquid. The materials are placed in a milling vessel that is rotated at optimal speed such that the media cascades and reduces the drug particle size by impaction. The media used must have a high density as the energy for the particle reduction is provided by gravity and the mass of the attrition media. Following particle size reduction of the at least one corticosteroid, at least one antihistamine is added to the composition.

1. Corticosteroid Particle Size Reduction Using Milling

Media milling is a high energy milling process. Corticosteroid, surface stabilizer, and liquid are placed in a reservoir and re-circulated in a chamber comprising grinding media and a rotating shaft/impeller. The rotating shaft agitates the grinding media which subjects the corticosteroid particles to impaction and sheer forces, thereby reducing the corticosteroid particle size.

The corticosteroid can be added to a liquid media in which it is essentially insoluble to form a premix. The surface stabilizer can be present in the premix or it can be added to the corticosteroid dispersion following particle size reduction. The premix can be used directly by subjecting it to mechanical means to reduce the average corticosteroid particle size in the dispersion to less than about 2000 nm. It is preferred that the premix be used directly when a ball mill is used for attrition. Alternatively, the corticosteroid and at least one surface stabilizer can be dispersed in the liquid media using suitable agitation, e.g., a Cowles type mixer, until a homogeneous dispersion is observed in which there are no large corticosteroid agglomerates visible to the naked eye. It is preferred that the premix be subjected to such a pre-milling dispersion step when a re-circulating media mill is used for attrition.

The mechanical means applied to reduce the corticosteroid particle size can take the form of a dispersion mill. Suitable dispersion mills include a ball mill, an attritor mill, a vibratory mill, and media mills such as a sand mill and a bead mill. A media mill is preferred due to the relatively shorter milling time required to provide the desired reduction in particle size. For media milling, the apparent viscosity of the premix is preferably from about 100 to about 1000 centipoise, and for ball milling the apparent viscosity of the premix is preferably from about 1 up to about 100 centipoise. Such ranges tend to afford an optimal balance between efficient corticosteroid particle size reduction and media erosion.

The corticosteroid attrition time can vary widely and depends primarily upon the particular mechanical means and processing conditions selected. For ball mills, processing times of up to five days or longer may be required. Alternatively, processing times of less than 1 day (residence times of one minute up to several hours) are possible with the use of a high shear media mill.

The corticosteroid particles can be reduced in size at a temperature which does not significantly degrade the corticosteroid molecule. Processing temperatures of less than about 30 to less than about 40° C. are ordinarily preferred. If desired, the processing equipment can be cooled with conventional cooling equipment. Control of the temperature, e.g., by jacketing or immersion of the milling chamber in ice water, is contemplated. Generally, the method of the invention is conveniently carried out under conditions of ambient temperature and at processing pressures which are safe and effective for the milling process. Ambient processing pressures are typical of ball mills, attritor mills, and vibratory mills.

Grinding Media

The grinding media for the corticosteroid particle size reduction step can be selected from rigid media preferably spherical or particulate in form having an average size less than about 3 mm and, more preferably, less than about 1 mm. Such media desirably can provide the particles of the invention with shorter processing times and impart less wear to the milling equipment. The selection of material for the grinding media is not believed to be critical. Zirconium oxide, such as 95% ZrO stabilized with magnesia, zirconium silicate, ceramic, stainless steel, titania, alumina, 95% ZrO stabilized with yttrium, glass grinding media, and polymeric grinding media are exemplary grinding materials.

The grinding media can comprise particles that are preferably substantially spherical in shape, e.g., beads, consisting essentially of polymeric resin or other suitable material. Alternatively, the grinding media can comprise a core having a coating of a polymeric resin adhered thereon. The polymeric resin can have a density from about 0.8 to about 3.0 g/cm$^3$.

In general, suitable polymeric resins are chemically and physically inert, substantially free of metals, solvent, and monomers, and of sufficient hardness and friability to enable them to avoid being chipped or crushed during grinding. Suitable polymeric resins include crosslinked polystyrenes, such as polystyrene crosslinked with divinylbenzene; styrene copolymers; polycarbonates; polyacetals, such as Delrin® (E.I. du Pont de Nemours and Co.); vinyl chloride polymers and copolymers; polyurethanes; polyamides; poly(tetrafluoroethylenes), e.g., Teflon® (E.I. du Pont de Nemours and Co.), and other fluoropolymers; high density polyethylenes; polypropylenes; cellulose ethers and esters such as cellulose acetate; polyhydroxymethacrylate; polyhydroxyethyl acrylate; and silicone-containing polymers such as polysiloxanes and the like. The polymer can be biodegradable. Exemplary biodegradable polymers include poly(lactides), poly(glycolide) copolymers of lactides and glycolide, polyanhydrides, poly(hydroxyethyl methacylate), poly(imino carbonates), poly(N-acylhydroxyproline)esters, poly(N-palmitoyl hydroxyproline) esters, ethylene-vinyl acetate copolymers, poly(orthoesters), poly(caprolactones), and poly(phosphazenes). For biodegradable polymers, contamination from the media itself advantageously can metabolize in vivo into biologically acceptable products that can be eliminated from the body.

The grinding media preferably ranges in size from about 0.01 to about 3 mm. For fine grinding, the grinding media is preferably from about 0.02 to about 2 mm, and more preferably from about 0.03 to about 1 mm in size.

In a preferred grinding process the corticosteroid particles are made continuously. Such a method comprises continuously introducing the corticosteroid active into a milling chamber, contacting the compounds with grinding media while in the chamber to reduce the particle size, and continuously removing the nanoparticulate active from the milling chamber.

The grinding media is separated from the milled nanoparticulate corticosteroid using conventional separation techniques, in a secondary process such as by simple filtration, sieving through a mesh filter or screen, and the like. Other separation techniques such as centrifugation may also be employed.

Sterile Product Manufacturing

Development of injectable compositions requires the production of a sterile product. The manufacturing process of the present invention is similar to typical known manufacturing processes for sterile suspensions. A typical sterile suspension manufacturing process flowchart is as follows:

(Media Conditioning)

↓

Compounding

↓

Particle Size Reduction

↓

Vial Filling

↓

(Lyophilization) and/or (Terminal Sterilization)

As indicated by the optional steps in parentheses, some of the processing is dependent upon the method of particle size reduction and/or method of sterilization. For example, media conditioning is not required for a milling method that does not use media. If terminal sterilization is not feasible due to chemical and/or physical instability, aseptic processing can be used.

2. Corticosteroid Particle Size Reduction Using Homogenization

Homogenization is a technique that does not use milling media. Corticosteroid, surface stabilizer, and liquid (or drug and liquid with the surface stabilizer added after particle size reduction) constitute a process stream propelled into a process zone, which in the Microfluidizer® is called the Interaction Chamber. The product to be treated is inducted into the pump, and then forced out. The priming valve of the Microfluidizer® purges air out of the pump. Once the pump is filled with product, the priming valve is closed and the product is forced through the interaction chamber. The geometry of the interaction chamber produces powerful forces of sheer, impact, and cavitation which are responsible for corticosteroid particle size reduction. Specifically, inside the interaction chamber, the pressurized product is split into two streams and accelerated to extremely high velocities. The formed jets are then directed toward each other and collide in the interaction zone. The resulting product has very fine and uniform particle or droplet size. The Microfluidizer® also provides a heat exchanger to allow cooling of the product. U.S. Pat. No. 5,510,118, which is specifically incorporated by reference, refers to a process using a Microfluidizer.®

3. Corticosteroid Particle Size Reduction Using Precipitation

Another method of forming the desired nanoparticle corticosteroid dispersion is by microprecipitation. This is a method of preparing stable dispersions of nanoparticulate particles of the composition according to the invention in the presence of one or more surface stabilizers and one or more colloid stability enhancing surface active agents free of any trace toxic solvents or solubilized heavy metal impurities. Such a method comprises, for example, (1) dissolving the corticosteroid composition according to the invention, in a suitable solvent with mixing; (2) adding the formulation from step (1) with mixing to a solution comprising at least one surface stabilizer to form a clear solution; and (3) precipitating the formulation from step (2) with mixing using an appropriate nonsolvent. The method can be followed by removal of any formed salt, if present, by dialysis or diafiltration and concentration of the dispersion by conventional means. The resultant nanoparticulate corticosteroid composition can be combined with at least one antihistamine and then utilized in liquid nebulizers or processed to form a dry powder for use in a DPI or pMDI.

4. Non-Aqueous Non-Pressurized Milling System

In a non-aqueous, non-pressurized milling system, a non-aqueous liquid having a vapor pressure of about 1 atm or less at room temperature and in which the nanoparticulate corticosteroid composition is essentially insoluble is used as a wet milling media to make a nanoparticulate corticosteroid composition. In such a process, a slurry comprised of the corticosteroid and surface stabilizer is milled in the non-aqueous media to generate a nanoparticulate corticosteroid composition. Examples of suitable non-aqueous media include ethanol, trichloromonofluoromethane, (CFC-11), and dichlorotetrafluoroethane (CFC-114). An advantage of using CFC-11 is that it can be handled at only marginally cool room temperatures, whereas CFC-114 requires more controlled conditions to avoid evaporation. Upon completion of milling the liquid media may be removed and recovered under vacuum or heating, resulting in a dry nanoparticulate corticosteroid composition. The dry nanoparticulate corticosteroid composition may then be filled into a suitable container and charged with a final propellant. Exemplary final product propellants, which ideally do not contain chlorinated hydrocarbons, include HFA-134a (tetrafluoroethane) and HFA-227 (heptafluoropropane). While non-chlorinated propellants may be preferred for environmental reasons, chlorinated propellants may also be used in this aspect of the invention.

5. Non-Aqueous Pressurized Milling System

In a non-aqueous, pressurized milling system, a non-aqueous liquid media having a vapor pressure significantly greater than 1 atm at room temperature is used in the milling process to make a nanoparticulate corticosteroid composition. If the milling media is a suitable halogenated hydrocarbon propellant, the resultant nanoparticulate corticosteroid dispersion may be filled directly into a suitable pMDI container (following the addition of at least one antihistamine). Alternately, the milling media can be removed and recovered under vacuum or heating to yield a dry composition comprised of a nanoparticulate corticosteroid composition. Following the addition of at least one antihistamine, this composition can then be filled into an appropriate container and charged with a suitable propellant for use in a pMDI.

6. Methods of Making Aerosol Formulations

An antihistamine/nanoparticulate corticosteroid composition according to the invention for aerosol administration can be made by, for example, by:

(1) nebulizing an aqueous dispersion of an antihistamine/nanoparticulate corticosteroid composition according to the invention, wherein the composition of the invention comprises at least one antihistamine, at least one nanoparticulate corticosteroid, and at least one surface stabilizer, wherein the nanoparticulate corticosteroid is obtained by grinding, homogenization, precipitation, or supercritical fluid particle generation techniques;

(2) aerosolizing a dry powder of aggregates of an antihistamine/nanoparticulate corticosteroid composition according to the invention, comprising at least one antihistamine, at least one nanoparticulate corticosteroid, and at least one surface stabilizer (the aerosolized composition may additionally contain a diluent), wherein the nanoparticulate corticosteroid is obtained by grinding, homogenization, precipitation, or supercritical fluid particle generation techniques; or (3) aerosolizing a suspension of an antihistamine/nanoparticulate corticosteroid aggregates of a composition according to the invention in a non-aqueous propellant, wherein the composition of the invention comprises at least one antihistamine, at least one nanoparticulate corticosteroid, and at least one surface stabilizer, wherein the nanoparticulate corticosteroid is obtained by grinding, homogenization, precipitation, or supercritical fluid particle generation techniques. The aggregates of a nanoparticulate composition according to the invention and surface stabilizer, which may additionally comprise a diluent, can be made in a non-pressurized or a pressurized non-aqueous system. Concentrated aerosol formulations may also be made by such methods.

7. Spray-Dried Powder Aerosol Formulations

Spray drying is a process used to obtain a powder comprising nanoparticulate corticosteroid particles following particle size reduction in a liquid media. In general, spray-drying is used when the liquid media has a vapor pressure of less than about 1 atm at room temperature. A spray-dryer is a device which allows for liquid evaporation and powder collection. A liquid sample, either a solution or suspension, is fed into a spray nozzle. The nozzle generates droplets of the sample within a range of about 20 to about 100 µm in diameter which are then transported by a carrier gas into a drying chamber. The carrier gas temperature is typically between about 80 and about 200 degrees C. The droplets are subjected to rapid liquid evaporation, leaving behind dry particles which are collected in a special reservoir beneath a cyclone apparatus.

If the liquid sample consists of an aqueous dispersion of nanoparticulate corticosteroid and at least one surface stabilizer, the collected product will consist of spherical aggregates of nanoparticulate corticosteroid and surface stabilizer. If the liquid sample comprises an aqueous dispersion of nanoparticulate corticosteroid and surface stabilizer in which an inert diluent material was dissolved (such as lactose or mannitol), the collected product will consist of diluent (e.g., lactose or mannitol) particles which comprise an embedded nanoparticulate corticosteroid composition. At least one antihistamine can be added to the nanoparticulate corticosteroid dispersion either before, during, or after spray drying. The final size of the collected product can be controlled and depends on the concentration of the nanoparticulate corticosteroid composition, antihistamine, and/or diluent in the liquid sample, as well as the droplet size produced by the spray-dryer nozzle. For deep lung delivery it is desirable for the collected product size to be less than about 2 microns in diameter, for delivery to the conducting airways it is desirable for the collected product size to be about 2 to about 6 microns in diameter, and for nasal delivery a collected product size of about 5 to about 100 µm is preferred. Collected products may then be used in conventional DPIs for pulmonary or nasal delivery, dispersed in propellants for use in pMDIs, or the particles may be reconstituted in water for use in nebulizers.

In some instances, it may be desirable to add an inert carrier to the spray-dried material to improve the metering properties of the final product. This may especially be the case when the spray dried powder is very small (less than about 5 microns) or when the intended dose is extremely small, whereby dose metering becomes difficult. In general, such carrier particles (also known as bulking agents) are too large to be delivered to the lung and simply impact the mouth and throat and are swallowed. Such carriers typically consist of sugars such as lactose, mannitol, or trehalose. Other inert materials, including polysaccharides and cellulosics, may also be useful as carriers.

Spray-dried powders comprising an antihistamine/nanoparticulate corticosteroid composition according to the invention may used in conventional DPIs, dispersed in propellants for use in pMDIs, or reconstituted in a liquid media for use with nebulizers.

8. Freeze-Dried Nanoparticulate Compositions

For a composition according to the invention that is denatured or destabilized by heat, such as having a low melting point (i.e., about 70 to about 150 degrees C.), or, for example, biologics, sublimation is preferred over evaporation to obtain a dry powder antihistamine/nanoparticulate corticosteroid composition. This is because sublimation avoids the high process temperatures associated with spray-drying. In addition, sublimation, also known as freeze-drying or lyophilization, can increase the shelf stability of a composition according to the invention, particularly for biological products. Freeze-dried particles can also be reconstituted and used in nebulizers. Aggregates of a freeze-dried antihistamine/nanoparticulate corticosteroid composition according to the invention can be blended with either dry powder intermediates or used alone in DPIs and pMDIs for either nasal or pulmonary delivery.

Sublimation involves freezing the product and subjecting the sample to strong vacuum conditions. This allows for the formed ice to be transformed directly from a solid state to a vapor state. Such a process is highly efficient and, therefore, provides greater yields than spray-drying. The resultant freeze-dried product comprises the antihistamine/nanoparticulate corticosteroid composition according to the invention. The composition according to the invention is typically present in an aggregated state and can be used for inhalation alone (either pulmonary or nasal), in conjunction with diluent materials (lactose, mannitol, etc.), in DPIs or pMDIs, or reconstituted for use in a nebulizer.

F. Method of Treatment

Yet another aspect of the invention provides a method of treating a mammal, including a human, using the antihistamine/nanoparticulate corticosteroid compositions of the invention for the prophylaxis or treatment of respiratory-related illnesses such as asthma, emphysema, respiratory distress syndrome, chronic bronchitis, cystic fibrosis, chronic obstructive pulmonary disease, organ-transplant rejection, tuberculosis and other infections of the lung, fugal infections, respiratory illness associated with acquired immune deficiency syndrome, oncology, and systemic administration of an anti-emetic, analgesic, cardiovascular agent, etc. The formulations and method result in improved lung and nasal surface area coverage by the administered composition according to the invention.

Such methods comprise the step of administering to a subject a therapeutically effective amount of the antihistamine/nanoparticulate corticosteroid composition of the invention via any suitable method.

In one embodiment of the invention, the compositions of the invention are administered via an aerosol dosage form. The aerosols of the invention, both aqueous and dry powder, are particularly useful in the treatment of respiratory-related illnesses such as asthma, emphysema, respiratory distress syndrome, chronic bronchitis, cystic fibrosis, chronic obstructive pulmonary disease, organ-transplant rejection, tuberculosis and other infections of the lung, fugal infections, respiratory illness associated with acquired immune deficiency syndrome, oncology, and systemic administration of an anti-emetic, analgesic, cardiovascular agent, etc. The formulations and method result in improved lung and nasal surface area coverage by the administered composition according to the invention One of ordinary skill will appreciate that effective amounts of an antihistamine and corticosteroid can be determined empirically and can be employed in pure form or, where such forms exist, in pharmaceutically acceptable salt, ester, or prodrug form. The selected dosage level therefore depends upon the desired therapeutic effect, the route of administration, the potency of the administered antihistamine and corticosteroid, the desired duration of treatment, and other factors.

Dosage unit compositions may contain such amounts of such submultiples thereof as may be used to make up the daily dose. It will be understood, however, that the specific dose level for any particular patient will depend upon a variety of factors: the type and degree of the cellular or physiological response to be achieved; activity of the specific agent or composition employed; the specific agents or composition employed; the age, body weight, general health, sex, and diet of the patient; the time of administration, route of administration, and rate of excretion of the agent; the duration of the treatment; drugs used in combination or coincidental with the specific agent; and like factors well known in the medical arts.

The following examples are given to illustrate the invention. It should be understood, however, that the spirit and scope of the invention is not to be limited to the specific conditions or details described in these examples but should only be limited by the scope of the claims that follow. All references identified herein, including U.S. patents, are hereby expressly incorporated by reference.

All formulation components were obtained commercially. Light scattering particle size measurements were performed on a Horiba LA-910 Laser Scattering Particle Size Distribution Analyzer (Horiba Instruments, Inc., Irvine, Calif.). Particle size distribution data are based on volume statistics.

Example 1

The purpose of this example was to prepare a nanoparticulate formulation of triamcinolone acetonide.

Triamcinolone acetonide drug substance (1.12 g) (PMRS) was combined with 8.95 g of a 5% hydroxypropylmethyl cellulose (HPMC) solution (Pharmacoat® 603; Shin-Etsu), 0.24 g of a 5% docusate sodium solution, and 12.08 g of sterile water for injection USP. The coarse slurry was milled in a NanoMill-01 machine (U.S. Pat. No. 6,431,478; Elan Drug Delivery (King of Prussia, Pa.)) equipped with a 50 mL chamber and containing 0.5 mm crosslinked polystyrene milling media (PolyMill-500; Dow Chemical) at 1333 rpm for 60 minutes (89% media load). During processing, chill water (approximately 5° C.) was circulated through the jacket of the mill chamber.

The final composition of the harvested dispersion was 5% triamcinolone acetonide, 2% HPMC, and 0.05% docusate sodium (all values w/w basis). The resulting dispersion had a mean triamcinolone acetonide particle size of 294 nm, with a D50 of 282 nm, a D90 of 407 nm, and a D95 of 457 nm. After 1 minute of sonication, the dispersion had a mean triamcinolone acetonide particle size of 292 nm with a D50 of 281 nm, a D90 of 401 nm, and a D95 of 446 nm. Similar particle size measurements following sonication indicate the absence of aggregates of triamcinolone acetonide. Such aggregates are undesirable.

The example demonstrates the successful preparation of a nanoparticulate triamcinolone acetonide composition, as the resulting D50 triamcinolone acetonide particle size was less than 2 microns.

Example 2

The purpose of this example was to prepare a nanoparticulate formulation of budesonide.

Budesonide drug substance (1.11 g) (Sicor Pharmaceuticals, Inc.) was combined with 0.13 g of polysorbate 80 and 21.40 g of sterile water for injection USP. The coarse slurry was milled in a NanoMill-01 machine equipped with a 50 mL chamber and containing 0.5 mm crosslinked polystyrene milling media (PolyMill-500; Dow Chemical) at 1333 rpm for 60 minutes (89% media load). During processing, chill water (approximately 5° C.) was circulated through the jacket of the mill chamber.

The final composition of the harvested dispersion was 5% budesonide, 0.5 polysorbate 80 (all values w/w basis). The resulting dispersion had a mean budesonide particle size of 287 nm with a D50 of 277 nm, a D90 of 389 nm, and a D95 of 437 nm. After 1 minute of sonication, the dispersion had a mean budesonide particle size of 327 nm, with a D50 of 318 nm, a D90 of 421 nm, and a D95 of 458 nm. Similar particle size measurements following sonication indicate the absence of aggregates of budesonide. Such aggregates are undesirable.

The example demonstrates the successful preparation of a nanoparticulate budesonide composition, as the resulting D50 budesonide particle size was less than 2 microns.

Example 3

The purpose of this example was to prepare a nanoparticulate formulation of fluticasone propionate.

Fluticasone propionate drug substance (1.12 g) (Dey Laboratories, Inc.) was combined with 8.95 g of a 5% povidone solution (Plasdone® K29-32; ISP), 0.23 g of a 5% sodium lauryl sulfate solution, and 12.09 g of sterile water for injection USP. The coarse slurry was milled in a NanoMill-01 machine equipped with a 50 mL chamber and containing 0.5 mm crosslinked polystyrene milling media (PolyMill-500; Dow Chemical) at 1333 rpm for 60 minutes (89% media load). During processing, chill water (approximately 5° C.) was circulated through the jacket of the mill chamber.

The final composition of the harvested dispersion was 5% fluticasone propionate, 2% povidone K29-32, and 0.05% sodium lauryl sulfate (all values w/w basis). The resulting dispersion had a mean fluticasone propionate particle size of 150 nm, with a D50 of 134 nm, a D90 of 251 nm, and a D95 of 298 nm. After 1 minute of sonication, the dispersion had a mean fluticasone propionate particle size of 165 nm, with a D50 of 151 nm, a D90 of 253 nm, and a D95 of 291 nm. Similar particle size measurements following sonication indicate the absence of aggregates of fluticasone propionate. Such aggregates are undesirable.

The example demonstrates the successful preparation of a nanoparticulate fluticasone propionate composition, as the resulting D50 fluticasone propionate particle size was less than 2 microns.

Example 4

The purpose of this example was to prepare and characterize a composition comprising a nanoparticulate corticosteroid and an antihistamine.

Nanoparticulate triamcinolone acetonide (0.40 g; Example 1) was combined with a 1.25% azelastine hydrochloride solution (1.60 g) to yield a 2.00 g sample comprising 1% triamcinolone acetonide and 1% azelastine hydrochloride (all values w/w).

Following combination of the corticosteroid and antihistamine, the particle size of the corticosteroid was measured. The initial mean particle size for triamcinolone acetonide was 577 nm, with a D50 of 350 nm, a D90 of 1263 nm, and a D95 of 1811 nm. After 1 minute of sonication, the triamcinolone acetonide nanoparticles had a mean size of 425 nm, with a D50 of 333 nm, a D90 of 748 nm, and a D95 of 1034 nm.

This example demonstrates the successful preparation of a composition comprising a nanoparticulate corticosteroid and an antihistamine, as following combination of the two active agents the nanoparticulate corticosteroid retained a D50 particle size of less than 2 microns.

Example 5

The purpose of this example was to prepare and characterize a formulation comprising a nanoparticulate corticosteroid and an antihistamine.

Nanoparticulate triamcinolone acetonide (0.40 g; Example 1) was combined with a 1.25% azelastine hydrochloride solution (0.16 g) and water (1.44 g) to yield a 2.00 g sample comprising 1% triamcinolone acetonide and 0.1% azelastine hydrochloride (all values w/w).

Following combination of the corticosteroid and antihistamine, the particle size of the corticosteroid was measured. The initial mean particle size for triamcinolone acetonide was 990 nm, with a D50 of 312 nm, a D90 of 834 nm, and a D95 of 6527 nm. After 1 minute of sonication, the triamcinolone acetonide nanoparticles had a mean size of 309 nm, with a D50 of 295 nm, a D90 of 433 nm, and a D95 of 490 nm. Similar particle size measurements following sonication indicate the absence of aggregates of fluticasone propionate. Such aggregates are undesirable.

This example demonstrates the successful preparation of a composition comprising a nanoparticulate corticosteroid and an antihistamine, as following combination of the two active agents the nanoparticulate corticosteroid retained a D50 particle size of less than 2 microns. However, this formulation is not as preferred as that given in Example 4, as the D90 particle size of 6527 prior to sonication, and the D90 particle size of 490 nm following 1 minute of sonication, indicates that several aggregates of triamcinolone acetonide are present in the composition.

Example 6

The purpose of this example was to prepare and characterize a formulation comprising a nanoparticulate corticosteroid and an antihistamine.

Nanoparticulate triamcinolone acetonide (0.10 g; Example 1) was combined with a 1.25% azelastine hydrochloride solution (4.00 g) and water (0.90 g) to yield a 5.00 g sample comprising 0.1% triamcinolone acetonide and 1% azelastine hydrochloride (all values w/w).

Following combination of the corticosteroid and antihistamine, the particle size of the corticosteroid was measured. The initial mean triamcinolone acetonide particle size was 158,669 nm, with a D50 of 129,570 nm, a D90 of 363,714 nm, and a D95% of 436,656 nm. After 1 minute of sonication, the triamcinolone acetonide nanoparticles had a mean size of 642 nm, with a D50 of 318 nm, a D90 of 618 nm, and a D95 of 2132 nm. Similar particle size measurements following sonication indicate the absence of aggregates of fluticasone propionate. Such aggregates are undesirable.

As the resulting composition comprised a corticosteroid composition having a D50 particle size of greater than about 2 microns prior to sonication, this particular combination of antihistamine and nanoparticulate corticosteroid, at the concentrations of corticosteroid and antihistamine utilized, was unsuccessful.

Example 7

The purpose of this example was to prepare and characterize a formulation comprising a nanoparticulate corticosteroid and an antihistamine.

Nanoparticulate triamcinolone acetonide (0.10 g; Example 1) was combined with a 1.25% azelastine hydrochloride solution (0.40 g) and water (4.50 g) to yield a 5.00 g sample comprising 0.1% triamcinolone acetonide and 0.1% azelastine hydrochloride (all values w/w).

Following combination of the corticosteroid and antihistamine, the particle size of the corticosteroid was measured. The initial mean triamcinolone acetonide particle size was 56,732 nm, with a D50 of 10,634 nm, a D90 of 175,996 nm, and a D95 of 233,293 nm. After 1 minute of sonication, the triamcinolone acetonide nanoparticles had a mean size of 599 nm, with a D50 of 307 nm, a D90 of 550 nm, and a D95 of 1277 nm.

As the resulting composition comprised a corticosteroid composition having a D50 particle size of greater than about 2 microns prior to sonication, this particular combination of antihistamine and nanoparticulate corticosteroid, at the concentrations of corticosteroid and antihistamine utilized, was unsuccessful.

Example 8

The purpose of this example was to prepare and characterize a formulation comprising a nanoparticulate corticosteroid and an antihistamine.

Nanoparticulate budesonide (0.40 g; Example 2) was combined with a 1.25% azelastine hydrochloride solution (1.60 g) to yield a 2.00 g sample comprising 1% budesonide and 1% azelastine hydrochloride (all values w/w).

Following combination of the corticosteroid and antihistamine, the particle size of the corticosteroid was measured. The initial mean budesonide particle size was 306 nm, with a D50 of 292 nm, a D90 of 427 nm, and a D95 of 482 nm. After 1 minute of sonication, the budesonide particles had a mean size of 292 nm, with a D50 of 280 nm, a D90 of 401 nm, and a D95 of 446 nm.

This example demonstrates the successful preparation of a composition comprising a nanoparticulate corticosteroid and an antihistamine, as following combination of the two active agents the nanoparticulate corticosteroid retained a D50 particle size of less than 2 microns.

Example 9

The purpose of this example was to prepare and characterize a formulation comprising a nanoparticulate corticosteroid and an antihistamine.

Nanoparticulate budesonide (0.40 g; Example 2) was combined with a 1.25% azelastine hydrochloride solution (0.16 g) and water (1.44 g) to yield a 2.00 g sample comprising 1% budesonide and 0.1% azelastine hydrochloride (all values w/w).

Following combination of the corticosteroid and antihistamine, the particle size of the corticosteroid was measured. The initial mean budesonide particle size was 291 nm, with a D50 of 279 nm, a D90 of 398 nm, and a D95 of 443 nm. After 1 minute of sonication, the budesonide nanoparticles had a mean size of 286 nm, with a D50 of 276 nm, a D90 of 387 nm, and a D95 of 435 nm.

This example demonstrates the successful preparation of a composition comprising a nanoparticulate corticosteroid and an antihistamine, as following combination of the two active agents the nanoparticulate corticosteroid retained a D50 particle size of less than 2 microns.

Example 10

The purpose of this example was to prepare and characterize a formulation comprising a nanoparticulate corticosteroid and an antihistamine.

Nanoparticulate budesonide (0.10 g; Example 2) was combined with a 1.25% azelastine hydrochloride solution (4.00 g) and water (0.90 g) to yield a 5.00 g sample comprising 0.1% budesonide and 1% azelastine hydrochloride (all values w/w).

Following combination of the corticosteroid and antihistamine, the particle size of the corticosteroid was measured. The initial mean budesonide particle size was 116,502 nm, with a D50 of 122,099 nm, a D90 of 185,497 nm, and a D95 of 209,080 nm. After 1 minute of sonication, the budesonide nanoparticles had a mean size of 303 nm, with a D50 of 289 nm, a D90 of 422 nm, and a D95 of 477 nm.

As the resulting composition comprised a corticosteroid composition having a D50 particle size of greater than about 2 microns prior to sonication, this particular combination of antihistamine and nanoparticulate corticosteroid, at the concentrations of corticosteroid and antihistamine utilized, was unsuccessful.

Example 11

The purpose of this example was to prepare and characterize a formulation comprising a nanoparticulate corticosteroid and an antihistamine.

Nanoparticulate budesonide (0.10 g; Example 2) was combined with a 1.25% azelastine hydrochloride solution (0.40 g) and water (4.50 g) to yield a 5.00 g sample comprising 0.1% budesonide and 0.1% azelastine hydrochloride (all values w/w).

Following combination of the corticosteroid and antihistamine, the particle size of the corticosteroid was measured. The initial mean budesonide particle size was 308 nm, with a D50 of 294 nm, a D90 of 430 nm, and a D95 of 486 nm. After 1 minute of sonication, the budesonide nanoparticles had a mean size of 307 nm, with a D50 of 294 nm, a D90 of 428 nm, and a D95 of 482 nm.

This example demonstrates the successful preparation of a composition comprising a nanoparticulate corticosteroid and an antihistamine, as following combination of the two active agents the nanoparticulate corticosteroid retained a D50 particle size of less than 2 microns (both before and after sonication).

Example 12

The purpose of this example was to prepare and characterize a formulation comprising a nanoparticulate corticosteroid and an antihistamine.

Nanoparticulate fluticasone propionate (0.40 g; Example 3) was combined with a 1.25% azelastine hydrochloride solution (1.60 g) to yield a 2.00 g sample comprising 1% fluticasone propionate and 1% azelastine hydrochloride (all values w/w).

Following combination of the corticosteroid and antihistamine, the particle size of the corticosteroid was measured. The initial mean fluticasone propionate particle size was 2024 nm, with a D50 of 1166 nm, a D90 of 5086 nm, and a D95 of 6360 nm. After 1 minute of sonication, the fluticasone propionate nanoparticles had a mean size of 1996 nm, with a D50 of 958 nm, a D90 of 5136 nm, and a D95 of 6475 nm.

As the resulting composition comprised a corticosteroid composition having a D50 particle size of greater than about 2 microns prior to sonication, this particular combination of antihistamine and nanoparticulate corticosteroid, at the concentrations of corticosteroid and antihistamine utilized, was unsuccessful.

Example 13

The purpose of this example was to prepare and characterize a formulation comprising a nanoparticulate corticosteroid and an antihistamine.

Nanoparticulate fluticasone propionate (0.40 g; Example 3) was combined with a 1.25% azelastine hydrochloride solution (0.16 g) and water (1.44 g) to yield a 2.00 g sample comprising 1% fluticasone propionate and 0.1% azelastine hydrochloride (all values w/w).

Following combination of the corticosteroid and antihistamine, the particle size of the corticosteroid was measured. The initial mean fluticasone propionate particle size was 549 nm, with a D50 of 287 nm, a D90 of 422 nm, and a D95 of 552 nm. After 1 minute of sonication, the fluticasone propionate nanoparticles had a mean size of 217 nm, with a D50 of 210 nm, a D90 of 323 nm, and a D95 of 362 nm.

This example demonstrates the successful preparation of a composition comprising a nanoparticulate corticosteroid and an antihistamine, as following combination of the two active agents the nanoparticulate corticosteroid retained a D50 particle size of less than 2 microns (both before and after sonication).

Example 14

The purpose of this example was to prepare and characterize a formulation comprising a nanoparticulate corticosteroid and an antihistamine.

Nanoparticulate fluticasone propionate (0.10 g; Example 3) was combined with a 1.25% azelastine hydrochloride solution (4.00 g) and water (0.90 g) to yield a 5.00 g sample comprising 0.1% fluticasone propionate and 1% azelastine hydrochloride (all values w/w).

Following combination of the corticosteroid and antihistamine, the particle size of the corticosteroid was measured. The initial mean fluticasone propionate particle size was 177 nm, with a D50 of 165 nm, a D90 of 270 nm, and a D95 of 306 nm. After 1 minute of sonication, the fluticasone propionate nanoparticles had a mean size of 177 nm, with a D50 of 165 nm, a D90 of 271 nm, and a D95 of 307 nm.

This example demonstrates the successful preparation of a composition comprising a nanoparticulate corticosteroid and an antihistamine, as following combination of the two active agents the nanoparticulate corticosteroid retained a D50 particle size of less than 2 microns (both before and after sonication).

Example 15

The purpose of this example was to prepare and characterize a formulation comprising a nanoparticulate corticosteroid and an antihistamine.

Nanoparticulate fluticasone propionate (0.10 g; Example 3) was combined with a 1.25% azelastine hydrochloride solution (0.40 g) and water (4.50 g) to yield a 5.00 g sample comprising 0.1% fluticasone propionate and 0.1% azelastine hydrochloride (all values w/w).

Following combination of the corticosteroid and antihistamine, the particle size of the corticosteroid was measured. The initial mean fluticasone propionate particle size was 1298 nm, with a D50 of 340 nm, a D90 of 3752 nm, and a D95 of 5026 nm. After 1 minute of sonication, the fluticasone propionate nanoparticles had a mean size of 1355 nm, with a D50 of 380 nm, a D90 of 3769 nm, and a D95 of 4957 mm.

This example demonstrates the successful preparation of a composition comprising a nanoparticulate corticosteroid and an antihistamine, as following combination of the two active agents the nanoparticulate corticosteroid retained a D50 particle size of less than 2 microns (both before and after sonication).

It will be apparent to those skilled in the art that various modifications and variations can be made in the methods and compositions of the present invention without departing from the spirit or scope of the invention. Thus, it is intended that the present invention cover the modifications and variations of this invention provided they come within the scope of the appended claims and their equivalents.

What is claimed is:

1. A composition comprising: (a) at least one non-nanoparticulate azelastine; (b) at least one corticosteroid having an effective average particle size of less than 2000 nm; and (c) at least one surface stabilizer; wherein the azelastine is present at 0.1% (w/w) of the composition and the corticosteroid is present at 1% (w/w) of the composition, and wherein the corticosteroid is selected from the group consisting of triamcinolone, budesonide and fluticasone.

2. The composition of claim 1, wherein the corticosteroid is triamcinolone, and the surface stabilizer comprises hydroxypropylmethyl cellulose and docusate sodium.

3. The composition of claim 1, wherein the corticosteroid is budesonide, and the surface stabilizer comprises polysorbate 80.

4. The composition of claim 1, wherein the corticosteroid is fluticasone, and the surface stabilizer comprises povidone and sodium lauryl sulfate.

5. A composition comprising: (a) at least one non-nanoparticulate azelastine; (b) at least one corticosteroid having an effective average particle size of less than 2000 nm; and (c) at least one surface stabilizer; wherein the corticosteroid is triamcinolone, and wherein the composition comprises 1% azelastine and 1% triamcinolone (w/w), or 0.1% azelastine and 1% triamcinolone (w/w).

6. The composition of claim 5, wherein the surface stabilizer comprises hydroxypropylmethyl cellulose and docusate sodium.

7. A composition comprising: (a) at least one non-nanoparticulate azelastine; (b) at least one corticosteroid having an effective average particle size of less than 2000 nm; and (c) at least one surface stabilizer; wherein the corticosteroid is budesonide, and wherein the composition comprises amounts of azelastine and budesonide selected from the group consisting of: 1% azelastine and 1% budesonide (w/w), 0.1% azelastine and 0.1% budesonide (w/w), and 0.1% azelastine and 1% budesonide (w/w).

8. The composition of claim 7, wherein the surface stabilizer comprises polysorbate 80.

9. A composition comprising: (a) at least one non-nanoparticulate azelastine; (b) at least one corticosteroid having an effective average particle size of less than 2000 nm; and (c) at least one surface stabilizer; wherein the corticosteroid is fluticasone, and wherein the composition comprises amounts of azelastine and fluticasone selected from the group consisting of: 1% azelastine and 0.1% fluticasone (w/w), 0.1% azelastine and 1% fluticasone (w/w), and 0.1% azelastine and 0.1% fluticasone (w/w).

10. The composition of claim 9 wherein the surface stabilizer comprises povidone and sodium lauryl sulfate.

11. The composition of claim 1, claim 5, claim 7 or claim 9, wherein the corticosteroid particles have a size selected from the group consisting of less than 1900 nm, less than 1800 nm, less than 1700 nm, less than 1600 nm, less than 1500 nm, less than 1400 nm, less than 1300 nm, less than 1200 nm, less than 1100 nm, less than 1000 nm, less than 900 nm, less than 800 nm, less than 700 nm, less than 650 nm, less than 600 nm, less than 550 nm, less than 500 nm, less than 450 nm, less than 400 nm, less than 350 nm, less than 300 nm, less than 250 nm, less than 200 nm, less than 150 nm, less than 100 nm, less than 75 nm, and less than 50 nm.

12. The composition of claim 1, claim 5, claim 7 or claim 9, wherein the composition further comprises one or more pharmaceutically acceptable excipients, carriers, or a combination thereof.

13. The composition of claim 1, claim 5, claim 7 or claim 9, formulated into an aerosol dosage form, wherein the composition is suitable for aerosol administration of the azelastine and corticosteroid dosage in about 15 seconds or less.

14. The composition of claim 1, claim 5, claim 7 or claim 9, formulated into an aerosol dosage form and further comprising a propellant that is administered from a multi-dose inhaler.

15. The composition of claim 1, claim 5, claim 7 or claim 9, formulated into an aerosol dosage form, wherein the aerosol is formed from a liquid dispersion of droplets comprising the composition and the droplets have a mass median aerodynamic diameter selected from the group consisting of less than or equal to 100 microns, about 30 to about 60 microns, about 0.1 to about 10 microns, about 2 to about 6 microns, and less than 2 microns.

16. The composition of claim 1, claim 5, claim 7 or claim 9, formulated into an aerosol dosage form, wherein the aerosol is formed from a dry powder of aggregates of the composition, wherein the aggregates have a mass median aerodynamic diameter selected from the group consisting of less than or equal to 100 microns, about 30 to about 60 microns, about 0.1 to about 10 microns, about 2 to about 6 microns, and less than 2 microns.

17. A method of making an antihistamine and nanoparticulate corticosteroid composition comprising the steps of: (a) contacting particles of at least one corticosteroid with at least one surface stabilizer for a time and under conditions sufficient to provide a corticosteroid composition having an effective average particle size of less than 2,000 nm; and (b) adding at least one non-nanoparticulate antihistamine to the composition, wherein following addition of the antihistamine the corticosteroid retains an effective average particle size of less than 2000 nm; wherein the antihistamine is azelastine; wherein the azelastine is present at 0.1% (w/w) of the composition and the corticosteroid is present at 1% (w/w) of the composition; and wherein the corticosteroid is selected from the group consisting of triamcinolone, budesonide and fluticasone.

18. A method of making an antihistamine and nanoparticulate corticosteroid composition comprising the steps of: (a) contacting particles of at least one corticosteroid with at least one surface stabilizer for a time and under conditions sufficient to provide a corticosteroid composition having an effective average particle size of less than 2,000 nm; and (b) adding at least one non-nanoparticulate antihistamine to the composition, wherein following addition of the antihistamine the corticosteroid retains an effective average particle size of less than 2000 nm; wherein the antihistamine is azelastine, wherein the corticosteroid is triamcinolone, and wherein the composition comprises 1% azelastine and 1% triamcinolone (w/w), or 0.1% azelastine and 1% triamcinolone (w/w).

19. A method of making an antihistamine and nanoparticulate corticosteroid composition comprising the steps of: (a) contacting particles of at least one corticosteroid with at least one surface stabilizer for a time and under conditions sufficient to provide a corticosteroid composition having an effective average particle size of less than 2,000 nm; and (b) adding at least one non-nanoparticulate antihistamine to the composition, wherein following addition of the antihistamine the corticosteroid retains an effective average particle size of less than 2000 nm; wherein the antihistamine is azelastine, wherein the corticosteroid is budesonide, and wherein the composition comprises amounts of antihistamine and corticosteroid selected from the group consisting of: 1% azelastine and 1% budesonide (w/w), 0.1% azelastine and 0.1% budesonide (w/w), and 0.1% azelastine and 1% budesonide (w/w).

20. A method of making an antihistamine and nanoparticulate corticosteroid composition comprising the steps of: (a) contacting particles of at least one corticosteroid with at least one surface stabilizer for a time and under conditions sufficient to provide a corticosteroid composition having an effective average particle size of less than 2,000 nm; and (b) adding at least one non-nanoparticulate antihistamine to the composition, wherein following addition of the antihistamine the corticosteroid retains an effective average particle size of less than 2000 nm; wherein the antihistamine is azelastine, wherein the corticosteroid is fluticasone, and wherein the composition comprises amounts of antihistamine and corticosteroid selected from the group consisting of: 1% azelastine and 0.1% fluticasone (w/w), 0.1% azelastine and 1% fluticasone (w/w), and 0.1% azelastine and 0.1% fluticasone (w/w).

21. A method of administering to a patient in need thereof an antihistamine/nanoparticulate corticosteroid composition, comprising administering to the patient a therapeutically effective amount of a composition comprising: (a) at least one non-nanoparticulate azelastine; (b) at least one nanoparticulate corticosteroid having an effective average particle size of less than 2000 nm; and (c) at least one surface stabilizer; wherein the azelastine is present at 0.1% (w/w) of the composition and the corticosteroid is present at 1% (w/w) of the composition, and wherein the corticosteroid is selected from the group consisting of triamcinolone, budesonide and fluticasone.

22. A method of administering to a patient in need thereof an antihistamine/nanoparticulate corticosteroid composition, comprising administering to the patient a therapeutically effective amount of a composition comprising: (a) at least one non-nanoparticulate azelastine; (b) at least one nanoparticulate corticosteroid having an effective average particle size of less than 2000 nm; and (c) at least one surface stabilizer; wherein the corticosteroid is triamcinolone, and wherein the composition comprises 1% azelastine and 1% triamcinolone (w/w), or 0.1% azelastine and 1% triamcinolone (w/w).

23. A method of administering to a patient in need thereof an antihistamine/nanoparticulate corticosteroid composition, comprising administering to the patient a therapeutically effective amount of a composition comprising: (a) at least one non-nanoparticulate azelastine; (b) at least one nanoparticulate corticosteroid having an effective average particle size of less than 2000 nm; and (c) at least one surface stabilizer; wherein the corticosteroid is budesonide, and wherein the composition comprises amounts of antihistamine and corticosteroid selected from the group consisting of: 1% azelastine and 1% budesonide (w/w), 0.1% azelastine and 0.1% budesonide (w/w), and 0.1% azelastine and 1% budesonide (w/w).

24. A method of administering to a patient in need thereof an antihistamine/nanoparticulate corticosteroid composition, comprising administering to the patient a therapeutically effective amount of a composition comprising: (a) at least one non-nanoparticulate azelastine; (b) at least one nanoparticulate corticosteroid having an effective average particle size of less than 2000 nm; and (c) at least one surface stabilizer; wherein the corticosteroid is fluticasone, and wherein the composition comprises amounts of antihistamine and corticosteroid selected from the group consisting of: 1% azelastine and 0.1% fluticasone (w/w), 0.1% azelastine and 1% fluticasone (w/w), and 0.1% azelastine and 0.1% fluticasone (w/w).

* * * * *